US012138420B2

(12) United States Patent
Rey

(10) Patent No.: US 12,138,420 B2
(45) Date of Patent: Nov. 12, 2024

(54) FEEDING CAP, DRIVE HEAD, AND DRIVE SYSTEM

(71) Applicants: Adventia Pharma, S.L., Las Palmas de Gran Canarias (ES); Andrés Cabello Rey, Las Palmas de Gran Canarias (ES)

(72) Inventor: Andrés Cabello Rey, Las Palmas de Gran Canarias (ES)

(73) Assignee: Adventia Pharma, S.L. (ES)

( * ) Notice: Subject to any disclaimer, the term of this patent is extended or adjusted under 35 U.S.C. 154(b) by 653 days.

(21) Appl. No.: 17/424,729

(22) PCT Filed: Dec. 16, 2019

(86) PCT No.: PCT/EP2019/085358
§ 371 (c)(1),
(2) Date: Jul. 21, 2021

(87) PCT Pub. No.: WO2020/151880
PCT Pub. Date: Jul. 30, 2020

(65) Prior Publication Data
US 2022/0133986 A1 May 5, 2022

(30) Foreign Application Priority Data

Jan. 22, 2019 (WO) .................. PCT/ES2019/070028

(51) Int. Cl.
*A61M 5/142* (2006.01)
*A61J 1/14* (2023.01)
(Continued)

(52) U.S. Cl.
CPC ........ *A61M 5/14232* (2013.01); *A61J 1/1406* (2013.01); *A61J 15/0026* (2013.01);
(Continued)

(58) Field of Classification Search
CPC ........ A61M 2202/0482; A61M 5/1413; A61M 5/14232; A61M 5/16831; A61J 1/1418;
(Continued)

(56) References Cited

U.S. PATENT DOCUMENTS 4,273,260 A * 6/1981 Bush ................. A61M 5/00
604/207
5,062,775 A * 11/1991 Orth .................. A61M 60/554
417/477.3
(Continued)

FOREIGN PATENT DOCUMENTS

EP 1776942 A1 4/2007
EP 2359799 A1 8/2011
(Continued)

OTHER PUBLICATIONS

Interational Search Report for PCT/EP2019/085358 mailed Feb. 20, 2020; 2 pages.

*Primary Examiner* — Quynh-Nhu H. Vu
(74) *Attorney, Agent, or Firm* — Lerner David LLP

(57) ABSTRACT

The present invention is comprised in the sector of the industry dedicated to the manufacturing of medical supplies, particularly focusing on containers for the artificial feeding of enteral feeding products through a tube. In particular, the present invention relates to a closure cap for a container for supplying enteral feeding products by means of the drive of a drive head, and it also relates to a drive head that can be coupled to the cap for driving the supply of enteral feeding products contained in a container, and in turn to a drive system formed by said cap and drive head.

19 Claims, 19 Drawing Sheets

(51) Int. Cl.
  *A61J 15/00* (2006.01)
  *A61M 5/14* (2006.01)
  *A61M 5/168* (2006.01)

(52) U.S. Cl.
  CPC ...... *A61M 5/1413* (2013.01); *A61M 5/16822* (2013.01); *A61M 5/16831* (2013.01); *A61M 2202/0482* (2013.01)

(58) Field of Classification Search
  CPC ...... A61J 1/1412; A61J 1/1425; A61J 1/1481; A61J 1/1475; A61J 15/0026
  See application file for complete search history.

(56) References Cited

U.S. PATENT DOCUMENTS

| | | | | |
|---|---|---|---|---|
| 8,715,238 | B2* | 5/2014 | Silver | F04B 43/073 604/151 |
| 10,100,824 | B2* | 10/2018 | Tsoukalis | F04B 43/1253 |
| 10,335,347 | B2* | 7/2019 | Carrel | B65D 41/50 |
| 10,612,681 | B2* | 4/2020 | Gagne | F16K 7/07 |
| 2007/0112323 | A1 | 5/2007 | Daly | |
| 2011/0004161 | A1* | 1/2011 | Ito | A61M 5/14232 604/154 |
| 2012/0248111 | A1* | 10/2012 | Bear | B65D 47/06 220/212 |
| 2013/0037509 | A1* | 2/2013 | Rahimy | A61J 1/1418 215/250 |
| 2013/0180618 | A1* | 7/2013 | Py | A61J 1/1406 141/2 |
| 2014/0003984 | A1* | 1/2014 | Miyazaki | A61M 5/14232 417/474 |
| 2014/0081202 | A1* | 3/2014 | Tsoukalis | A61M 5/142 604/153 |
| 2015/0112265 | A1* | 4/2015 | Tsoukalis | F04B 13/00 604/151 |
| 2016/0123320 | A1* | 5/2016 | Tsoukalis | A61M 5/14232 417/477.2 |
| 2017/0258981 | A1* | 9/2017 | Franano | A61M 60/508 |

FOREIGN PATENT DOCUMENTS

| | | |
|---|---|---|
| EP | 3053618 A1 | 8/2016 |
| WO | 2014078404 A1 | 5/2014 |

* cited by examiner

FEEDING CAP, DRIVE HEAD, AND DRIVE SYSTEM

CROSS REFERENCE TO RELATED APPLICATIONS

The present application is a national phase entry under 35 U.S.C. § 371 of International Application No. PCT/EP2019/085358 filed Dec. 16, 2019, which claims priority from International Application No. PCT/ES2019/070028 filed on Jan. 22, 2019 the disclosures of which are incorporated herein by reference.

OBJECT

The present disclosure relates to the sector of the industry dedicated to the manufacturing of medical supplies, particularly focusing on containers for the artificial feeding of enteral feeding products through a tube. In particular, the present disclosure relates to a closure cap for a container for supplying enteral feeding products by means of the drive of a drive head, and it also relates to a drive head that can be coupled to the cap for driving the supply of enteral feeding products contained in a container, and in turn to a drive system formed by said cap and drive head.

BACKGROUND

Enteral feeding through a tube is a special feeding technique (also referred to as artificial feeding) which consists of delivering the different nutrients the patient needs through a feeding tube. The feeding tube is placed such that one end remains on the outside and the other end is inserted into the patient through the nose either to the digestive tract, bypassing buccal and esophageal ingestion stages, or directly to the jejunum.

To supply the products contained in the containers, syringes (known as bolus) or electromechanical infusion pumps are typically used. The pumps are usually peristaltic- or diaphragm-type pumps. In the first case, the product to be supplied must be transferred from the container to the syringe to then be driven through the tube of the patient. In the case of electromechanical pumps, the container is hung from a special hanger, connected to a feeding tube running along the entire circuit of the machine, and finally connected to the tube of the patient.

In the case of bolus infusion, gastrointestinal complications often arise due to an incorrect technique in delivery speed. Delivery must be performed at a low and constant speed, so it requires a certain time and expert handling usually by an assistant. There is also a need to take into account the high risk of product contamination as a result of transfers and handling. In the case of electromechanical pump infusion, the problem lies in the fact that this type of apparatus usually has a very high cost, so not all hospital centers or clinics have the required number of units. Generally, the patient is forced to remain hospitalized since outpatient treatment is not usually available. Another drawback of the known supply systems for enteral feeding lies in the fact that the patient has a very low mobility and autonomy while being connected to the infusion pump. Furthermore, the use of electromechanical pumps likewise requires a considerable level of handling experience and skill, both in handling the containers and feeding tubes and in handling the electronic apparatus.

To use the electromechanical pump, the user or assistant must connect the feeding tube to the container, partially filling up the drip, purging air from the feeding tube, placing the silicone section of the feeding tube in the rotor of the pump, connecting the feeding tube to the patient's tube itself, and operating the pump by means of the electronic programmer. This handling tends to be complicated for many patients, so a second person with adequate knowledge is often required, like in the case of bolus delivery.

On the other hand, containers incorporating therein a piezoelectric device-operated membrane pump have been previously proposed. In this case, the entire mechanism of the pump is contaminated by the product, so it must be disposed of completely after use together with the container of which it is part. The high cost involved in disposing of an entire pump after every use makes this alternative unfeasible. Another proposal has a semi-toric-type pump formed by two discs forming a channel through which the fluid driven out by rollers runs. The configuration of this proposal has various technical drawbacks: on one hand, it is impossible to achieve a leak-tight closure, so there is a high risk of product contamination and even leakages during use; on the other hand, all the parts making up the pump are again contaminated, so they cannot be reused without a high cleaning and sterilization cost. The design of said semi-toric pump even has an opening which allows the fluid to return to the container, so it would not be driven in any manner to the feeding tube. Therefore, the objective of the present invention is to resolve all these drawbacks and provide the patients subjected to this type of feeding with the possibility of being able to have a much simpler, easier-to-use, and more cost-effective drive system that can be found in any medical center and even allow the patients to use it in their own house with greater autonomy, and therefore allows reducing the hospitalization period of the patient.

In a first inventive aspect, the present disclosure provides a closure cap for a container for supplying enteral feeding products contained in said container by means of the drive of a drive head, the cap being adapted for being coupled to a drive head, characterized in that it comprises:

a first open cavity suitable for receiving therein products coming from inside the container, the first cavity comprising coupling means for the attachment of the cap with a neck of the container, a first outlet port of the first cavity, a second open cavity separated from the first cavity and configured with the opening in opposition to the opening of the first cavity, the second cavity comprising a second outlet port of the cap for supplying the product of the container, a support seating, a conduit providing fluid communication between the first outlet port of the first cavity and the second outlet port of the second cavity, the conduit comprising a first flexible conduit segment with a first region which is supported on the support seating and a second region which is arranged facing the first region in the first flexible conduit segment so as to allow rotary rollers of the drive head to press this second region against the support seating, such that when the cap is in the operating mode with the drive head the fluid contained inside the conduit is driven by the action of the rollers.

Terms such as "in the operating mode" or "when the cap or drive head is in the operating mode with one another" will be used throughout the description. The feeding cap is a device which supplies products when it is coupled to the drive head and the drive head itself operates the drive of said product. Nevertheless, the expression "in the operating mode" will be understood when both devices, i.e., the cap and the head, are working with respect to one another, given that they are interrelated devices.

The term elastic will be used throughout the description in relation to one or more conduits. Elastic will be interpreted as a property a body has of being elastically deformable and therefore having the capacity to recover the shape before deformation.

The present cap is intended for being coupled in a container storing therein enteral feeding products, and in turn for being coupled to a drive head to cooperate with the cap to supply said products. The present cap is understood to be a closure cap for the container, i.e., when the cap is coupled to the container, this container is closed by the cap. The cap comprises coupling means which facilitate and allow the attachment or coupling of the cap to a neck of the container.

The cap mainly comprises two cavities, a first cavity and a second cavity, each independent and separated from the other. Both cavities are open cavities, such that each cavity comprises an opening. The opening of the first cavity is arranged in opposition to the opening of the second cavity when both cavities are configuring the cap.

The first cavity is suitable for receiving therein the products coming from inside the container through its opening. When the cap is coupled to the neck of the container through the coupling means, the product contained in the container is poured into the opening of the first cavity. In turn, this first cavity comprises a first outlet port through which the product housed in the opening of this first cavity moves out to the second cavity of the cap. This first outlet port advantageously allows the passage of the product from the first cavity to the second cavity.

The second cavity is in fluid communication with the first cavity through a conduit, a flexible conduit as least in a segment for being driven by a drive head, arranged in this second cavity, particularly the conduit puts the first outlet port comprised in the first cavity in fluid connection with a second outlet port comprised in the second cavity. This second outlet port is understood to be an exit through which the product, coming from a container to which the cap is coupled, is supplied. The arrangement of the conduit in the second cavity advantageously allows transferring the product from the first cavity to the outside of the cap in order to supply same.

The flexible conduit segment is understood to be a tube made of a flexible material which can pressed by the action of the rollers of the drive head, thereby facilitating the driving of the fluid or product circulating through the inside of said conduit.

The second cavity further comprises a support seating suitable for supporting thereon the first flexible conduit segment. In other words, the support seating is understood to be according to a first embodiment a notch-type structure or according to a second embodiment a cylindrical band, configured for receiving said first flexible conduit segment. In particular, this first flexible conduit segment comprises a first region intended for being supported on the support seating, and a second region intended for being pressed by rotary rollers of the drive head, these regions being arranged facing one another. When the cap is coupled to the drive head, the rollers comprised in the drive head press the second region of the first flexible conduit segment, such that the first region of this flexible conduit segment which is supported on the support seating is pressed on this support seating.

In other words, when the cap is in the operating mode with the drive head, the fluid, the product coming from the container and circulating through the inside of the conduit, is driven through this conduit by the action of the rollers of the drive head, i.e., by the pressure exerted by the rollers on the second region of the first flexible conduit segment of the cap.

The cap being configured with two cavities and the flexible conduit segment being arranged inside the second cavity advantageously provide the cap with sufficient characteristics to prevent the content of the product to be supplied from being contaminated or from undergoing alterations of the contents. On one hand, this is achieved as a result of the sealing achieved in the first cavity when the cap is coupled to the neck of the container, and on the other hand, the separation of the cavities prevents the drive head from interfering with said product as it only comes into contact with the second cavity, and in this second cavity the product circulates through the inside of the conduit.

The present feeding cap advantageously allows the patient to self-supply nutritional feeding products, particularly enteral feeding products, in an autonomous manner. This self-supply is furthermore carried out in a quick and simple manner for the patient without having to handle the product contained in the original container in which it is stored, and furthermore without requiring an additional person with medical experience and skill to supply said product. In other words, the feeding cap is configured for the patient to self-supply the product without the presence of a medical assistant, i.e., the hospitalization period of a patient is furthermore reduced since the patient himself/herself can continue his/her nutritional feeding treatment from home.

In a particular embodiment, the first cavity is configured for receiving the neck of the container according to a longitudinal direction d, and the first flexible conduit segment of the conduit containing the first region and the second region extends in a plane transverse to direction d. Relative terms, such as upper, lower, vertical, horizontal, and other similar terms, will be used throughout the description in reference to the position and orientation of the present cap and head. In a particular example, the cap extends along a longitudinal direction d, the direction in which coupling of the container and of the head to the cap occurs. Nevertheless, "longitudinal direction d" will be understood to be a reference direction on which the container and the drive head are arranged when they are coupled to the cap. According to this longitudinal direction d, it will be understood that both cavities of the cap, in operative mode, are concentric to this longitudinal direction d. Furthermore, the first flexible conduit segment is arranged inside the second cavity contained in a plane perpendicular to longitudinal direction d. In turn, it will be understood that the first cavity of the feeding cap is oriented towards the neck of the container, and the second cavity of the cap is oriented towards the drive head. The second cavity of the cap is configured for receiving the drive head according to longitudinal direction d.

In a particular embodiment, the first flexible conduit segment of the conduit containing the first region and the second region has a directrix of a circular arc contained in a plane transverse to direction d.

In a particular embodiment, the main body of the cap is a frame comprising at least two frame segments extending according to longitudinal direction d:
a first frame segment comprising the first cavity and the coupling means for attaching the cap with a neck of the container, and
a second frame segment comprising the second cavity for housing the drive head.

The frame segments of the cap configure two spaces independent of one another, with one segment comprising the first cavity and the other segment comprising the second cavity. Advantageously, each configured space is isolated from the other space, particularly, the inside of the first cavity is isolated from the second cavity, and this thereby prevents the product to be supplied from being contaminated when it circulates through the cap.

In a particular embodiment, the second frame segment has a larger diameter than the first frame segment, and both frame segments are connected by a disc perpendicular to longitudinal direction d.

According to this embodiment, both frame segments are one after the other, connected by means of a disc, along the longitudinal direction d, this disc being contained in a plane transverse to this longitudinal direction.

The second frame segment and the disc form the second cavity the diameter of which is larger than the diameter of the first cavity forming the first frame segment. Nevertheless, in a particular embodiment the opening of the second cavity is of a larger size than the opening of the first cavity.

In a particular embodiment, the cap comprises a casing which houses therein the first frame segment and is supported on the peripheral area of the disc. This casing is understood to be an outer enveloping body which surrounds the first frame segment, the first cavity thereby being housed therein, such that the casing follows the opening of this first cavity. In other words, the casing comprises a hole matching the opening of the first cavity to allow the coupling of the container with the cap.

This casing advantageously protects the structure formed by the first frame segment of the cap from the outside thereof. Furthermore, the casing is supported on the peripheral area of the disc, such that the casing is circular and arranged concentric to longitudinal direction d.

In a particular embodiment, the casing can be coupled to the second frame segment through clipping with the peripheral area of the disc. This clipping system advantageously facilitates the coupling of the casing to the peripheral area of the disc in a simple and quick manner.

In a particular embodiment, the coupling means of the first cavity comprise a thread surface for attachment with the neck of the container by threading. This thread surface advantageously facilitates the coupling of the neck of the container to the cap by means of attaching this neck with the thread surface by threading. Furthermore, these coupling means seal the first cavity when the container is coupled to the cap, i.e., when the product contained in the container flows into the first cavity, this product is completely isolated from the outside.

In a particular embodiment, the support seating is a surface segment in the form of a band the directrix of which extends in a circle around a central axis and in a plane transverse to longitudinal direction d, this central axis being parallel to longitudinal direction d, wherein the section of this surface according to a plane going through the central axis is an arc-shaped segment.

The surface segment of the support seating, according to an embodiment, is understood to be an arc-shaped notch or open channel running along a plane transverse to longitudinal direction d or central axis, describing a circle according to the directrix of this notch. In a particular embodiment, the arc-shaped segment has normal direction corresponding to the surface of the support seating that is oblique and oriented towards the outside of the second cavity.

This orientation that is oblique and oriented towards the outside of the second cavity allows the flexible conduit to receive a drive head with oblique rollers, such that the entry and exit of the drive head is facilitated and such that, in the operating mode, the rollers do not generate a wedging which clamps and destroys the flexible conduit.

In a particular embodiment, the radius of curvature of the arc-shaped segment of the section of the surface of the support seating is greater than the radius of curvature of the cross section of the flexible conduit. This difference in size of the radius of curvature between the arc-shaped segment and the flexible conduit advantageously allows the flexible conduit to be housed in or supported on the arc-shaped segment defining the surface of the support seating, and the flexible conduit to automatically look for the most stable support so as to improve the drive function.

In a particular embodiment alternative to the two former embodiments, the support seating is a surface segment in the form of a cylindrical band housed in the second cavity. In a specific example, the support seating is on the inner wall of the second frame segment.

According to this embodiment, the drive head has rollers with axis of rotation that are parallel to the longitudinal direction. This arrangement avoids the shear stress of the first flexible conduit segment increasing the life of said segment. In a particular embodiment, the cap is characterized in that:

the exit of the first outlet port of the first cavity is outside a first frame segment, a second frame segment has a connection adaptor with an end inside the second cavity and the opposite end outside the second frame segment, wherein the cap comprises a second fluid connection conduit between the first outlet port of the first cavity and the outer end of the connection adaptor, and the conduit is connected to the inner end of the connection adaptor for fluid communication with the first outlet port.

In a particular embodiment, the connection adaptor is located after the support seating such that the first flexible conduit segment is arranged on the support seating and connected at the ends thereof to the outer and inner ends of the connection adaptor.

The arrangement of a connection adaptor in the second cavity advantageously holds the first flexible conduit segment in the second cavity. In turn, this connection adaptor allows connection between the second conduit and the first flexible conduit segment. In a particular embodiment, the second conduit is a flexible conduit.

In a particular embodiment, the cap comprises a third fluid connection conduit between the second outlet port and a connector. This third conduit allows fluid communication between the first flexible conduit segment and a connector. In other words, the third conduit is understood to be a conduit or tube arranged on the outside of the cap connected at one end to the second outlet port and at the other end to a connector. This connector is suitable for being connected or coupled to a tube of the patient.

In a particular embodiment, the third fluid connection conduit is a flexible conduit or tube. According to these embodiments, the flexible tubes can be replaced with new ones when the flexible material losses its properties or is deemed unfit, for example, due to the appearance of deposits which may affect hygiene.

In a particular embodiment, the second frame segment comprises at least one protrusion projecting in a radial direction with respect to longitudinal direction d to be fitted in at least one groove of the drive head, configuring a bayonet lock between the cap and the drive head.

This bayonet lock allows the patient to couple the drive head to the cap in a quick and simple manner. Furthermore, this lock allows keeping the cap fixed to the drive head while the product of interest is being supplied.

In a particular embodiment alternative to the former embodiment, the cap comprises linear guiding means perpendicular to the longitudinal direction d to be fitted with opposite linear guiding means of the drive head, configuring a linear bayonet lock between the cap and the drive head.

This embodiment is suitable for an embodiment of the cap wherein the linear bayonet lock has first insertion position and final locking position wherein in the final locking position the rotary rollers of the drive head are exerting a pressing force against the first flexible conduit segment. In this embodiment the rotary rollers do not exert an axial force highly reducing the shear stress of the first flexible conduit segment prolonging the life of the first flexible conduit segment. In a particular embodiment, the cap comprises a check valve for the entry of air from the second cavity to the first cavity.

In a more particular embodiment, the check valve is located between the first and second cavity. Advantageously, this check valve allows the entry of air into the first cavity and facilitates the pumping or drive of the product or fluid from the first cavity to the second cavity.

In a particular embodiment, the first cavity comprises perforation means for perforating a seal of the neck of the container when the cap is coupled to the neck. Advantageously, these perforation means facilitates opening the seal arranged in the neck of the container. In a particular embodiment, the perforation means comprise a protrusion with edges configured for breaking or tearing the seal.

In a particular embodiment, the conduit is a transparent flexible tube. The flexible conduit will be understood to be a plurality of conduits or conduit segments suitable for the circulation of the product to be supplied through the inside thereof. The fact that this conduit is a transparent flexible tube advantageously allows observing whether or not the product is circulating through the inside of said conduit.

In a particular embodiment, the flexible conduit formed by the first conduit segment, the second and third conduit, is a flexible silicone tube.

In a second inventive aspect, the present disclosure provides a drive head adapted for being coupled to a cap according to the first inventive aspect for driving the supply of enteral feeding products contained in a container through said cap when the cap is in the operating mode in the neck closing the container, characterized in that the drive head comprises:
one or more rotary rollers radially distributed around an axis of rotation E,
operating means for operating the rotation of the roller or rollers,
coupling means for fixing the cap with respect to the drive head, such that when the drive head is coupled to the cap in the operating mode, the roller or rollers are positioned with respect to the conduit of the cap such that these rollers exert pressure on a second region of a first flexible conduit segment of the cap to drive the product flowing through the inside of said conduit when the roller or rollers rotate around the axis of rotation E in the operating mode.

The operating means are responsible for operating the rotation or turning of the rollers around an axis of rotation E, this axis of rotation matching the central axis of the cap when the drive head is in the operating mode or coupled to the cap, and the axis of rotation E is also parallel with longitudinal direction d.

When the drive head is in the operating mode with the cap, as the rollers rotate around the axis of rotation E, these rollers press the second region of the first flexible conduit segment, thereby driving the product circulating through the inside of this first flexible conduit segment.

In particular, according to an embodiment, the rollers are arranged with an inclination matching the normal defined for the support seating of the feeding cap. According to an alternative embodiment, the rollers are arranged parallel to the longitudinal direction matching the normal defined for the cylindrical support seating of the cap.

The present drive head advantageously allows driving the product/fluid circulating through the inside of the flexible conduit of the cap to thereby facilitate the supply thereof to the patient. In particular, the arrangement of the rollers is such that it optimizes contact between these rollers and the first flexible conduit segment of the feeding cap, and in turn allows the drive head to be coupled to and decoupled from said feeding cap with ease.

In a particular embodiment, the operating means are a motor.

On the other hand, the coupling means advantageously allow keeping the drive head coupled to the cap while supplying the product to the patient, thereby preventing the cap from being separated from the drive head and the pumping or drive of the product from being interrupted or stopped, thereby stopping the supply of the product to the patient.

In a particular embodiment, the main body of the drive head comprises a casing comprising at least two casing segments extending according to a longitudinal direction d:
a first casing segment configured in the form of a cylindrical sector for housing the plurality of rollers, and
a second casing segment configured in the form of a closed cavity housing therein the operating means.

The first casing segment in the form of a cylindrical sector defines an open cavity in which the rollers are housed such that, by being open, this first casing segment allows the rollers to come into contact with the first flexible conduit segment of the cap when the drive head is coupled to the cap.

In a particular embodiment, the first casing segment is configured for receiving the feeding cap according to a length direction d.

In a particular embodiment, the first casing segment comprises at least one groove for receiving at least one protrusion of the feeding cap, configuring a bayonet lock between the cap according to an embodiment of the first inventive aspect and the drive head. Advantageously, the groove facilitates the insertion of the protrusion of the feeding cap, thereby allowing the coupling and fixing of the cap to the drive head in a quick and simple manner for the patient.

In a particular embodiment, the rollers are arranged on oblique shafts converging in the axis of rotation E, the oblique shafts being fixed to a roller frame configured for rotating around the axis of rotation E.

The drive head comprises a roller frame arranged along the axis of rotation E, such that each roller is fixed to this frame through its oblique shaft. The roller frame is the body responsible for rotation, and the rollers rotate along with the frame due to the fixing thereof to said frame through said oblique shafts.

In a particular embodiment, the linear bayonet lock has first insertion position and final locking position wherein in the final locking position the rotary rollers of the drive head are exerting a pressing force against the first flexible conduit segment.

This embodiment is suitable for the embodiment wherein the rollers are arranged parallel to the longitudinal direction matching the normal defined for the cylindrical support seating of the feeding cap. Nonetheless, the linear bayonet lock may also be combined with the specific embodiment where the rollers are arranged on oblique shafts converging in the axis of rotation E. In a more particular embodiment wherein the shafts of the rollers are in an oblique position, each oblique shaft is fixed to the roller frame by means of two clipping clamps arranged according to longitudinal direction d, with one clamp being located closer to the axis of rotation E than the opposite clamp such that the roller is arranged in an oblique position between both clipping clamps.

The fixing of the oblique shafts to the roller frame by means of a clamp clipping system advantageously allows replacing or exchanging the rollers, for example, when they are worn out or when it is of interest to replace them with new ones, or to facilitate cleaning the drive head.

In a particular embodiment, the drive head comprises an optoelectronic sensor configured for detecting whether product or air circulates through the inside of the conduit of the cap, such that when the drive head is in the operating mode with the cap, and the optoelectronic sensor detects that air circulates through the inside of the conduit of the cap, rotation of the rollers is stopped. The optoelectric sensor is in data communication with control means or an electronic system responsible for controlling the operation of the operating means, such that when the sensor detects that no product is circulating through the inside of the flexible conduit of the cap or that air is circulating, the controller immediately stops the rotation of the rollers. In particular, this sensor detects the passage of product through the inside of the conduit connecting with the tube of the patient.

Advantageously, the optoelectric sensor allows knowing if the product is circulating through the inside of the flexible conduit of the cap and, working together with the automatic control, it stops the operation of the drive head when necessary, i.e., when there is no more product to be supplied. In a particular embodiment, the optoelectronic sensor comprises holding means configured for partially holding the third conduit of the cap, wherein the optoelectronic sensor is furthermore configured for detecting if the conduit is held in the holding means when the drive head is in the operating mode with the feeding cap.

In a particular embodiment, the drive head comprises a display configured for showing the parameters measured by the optoelectric sensor.

Advantageously, the presence of this display allows the patient to view the parameters measured by the optoelectric sensor, as well as indications of whether or not the drive head is in operation. In a third inventive aspect, the present disclosure provides a drive system comprising a cap according to the first inventive aspect and a drive head according to the second inventive aspect. This drive system advantageously facilitates the supply of enteral feeding products, such that the patient him/herself can use this system without requiring an additional person or a person with medical experience.

As mentioned for the feeding cap and the drive head, these comprise coupling means for being coupled to one another. The fact that the components of the system can be coupled to one another allows reusing the drive head for different caps, as well as disposing of the cap that has been used and replacing it with a new one, to thereby enable supplying a new product. In other words, the present disclosure proposes a system for driving and supplying products for the patient which can be used as many times as desired by simply replacing the feeding cap for each use or product to be supplied.

The present drive system substantially simplifies and improves the nutritional product delivery method, such that the participation of another person becomes unnecessary. Furthermore, this system advantageously provides the patient with a high autonomy, which entails a significant savings in human resources in the health sector and facilitates outpatient treatment.

DESCRIPTION OF THE DRAWINGS

These and other features and advantages of the disclosure will be more clearly understood based on the following detailed description of a preferred embodiment given only by way of illustrative and non-limiting example in reference to the attached drawings.

DETAILED DESCRIPTION

Figure 1:
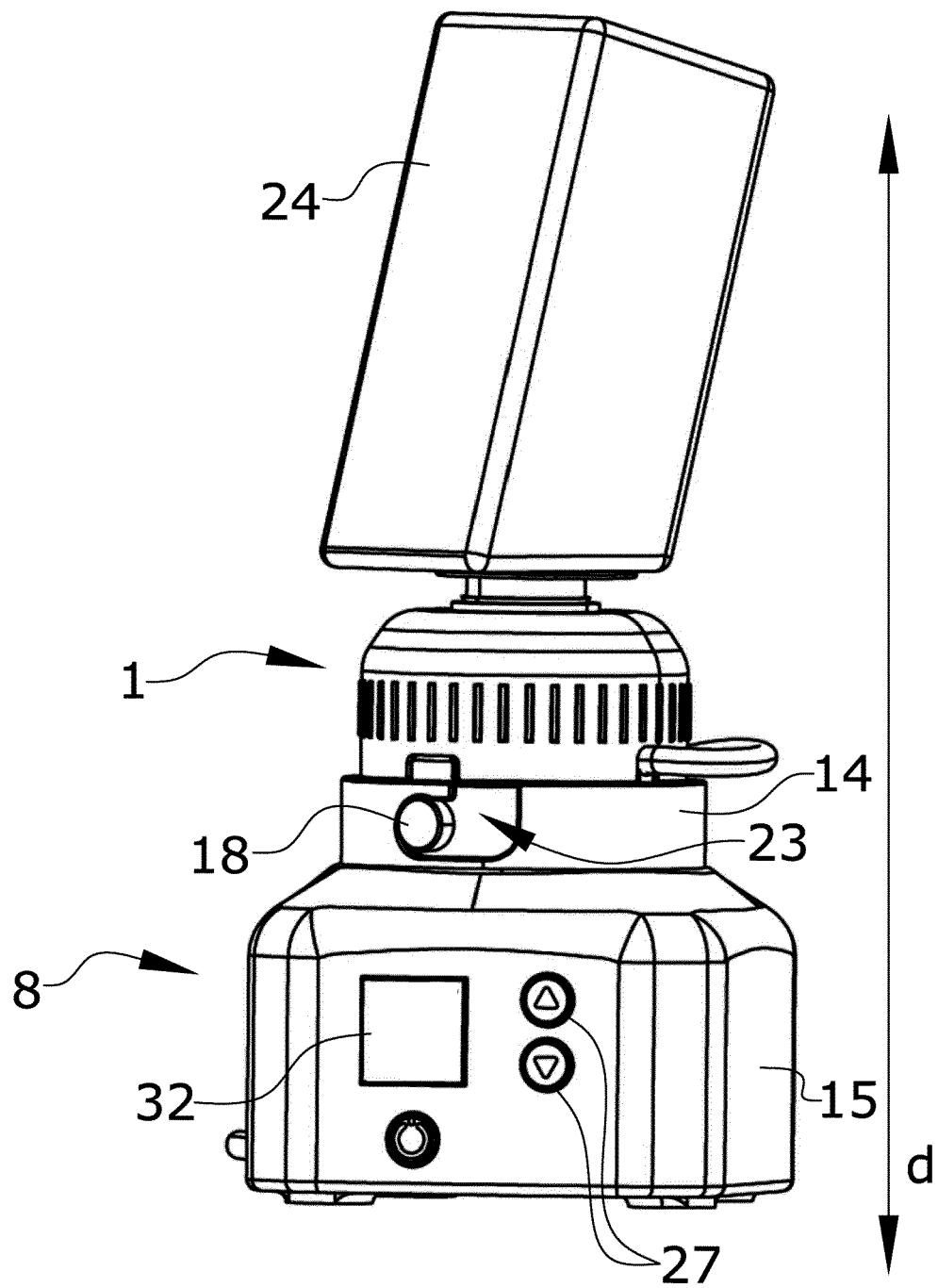
FIG. 1 shows a perspective view of the drive system coupled to a container according to a first embodiment of the present disclosure.

According to the third inventive aspect, the present disclosure relates to a drive system as shown in the lower part of FIG. 1. This drive system comprises a closure cap (1) coupled to a drive head (8). This FIG. 1 further shows a container (24) coupled to the feeding cap (1). This container (24) is suitable for storing enteral feeding products which are supplied to a patient through the drive system of the present disclosure.

The cap (1) receives the container (24) and the drive head (8) according to a longitudinal direction d. In other words, when the drive system is coupled to an enteral feeding container (24) or in the operating mode with said container (24), they are coupled following the longitudinal direction d. In particular, the cap (1) according to a first embodiment is coupled/fixed to the drive head (8) by means of the insertion of a protrusion (18) in a groove (23) of the said drive head (8), this groove (23) being arranged in a first casing segment (14) of the drive head (8).

Figure 2A:
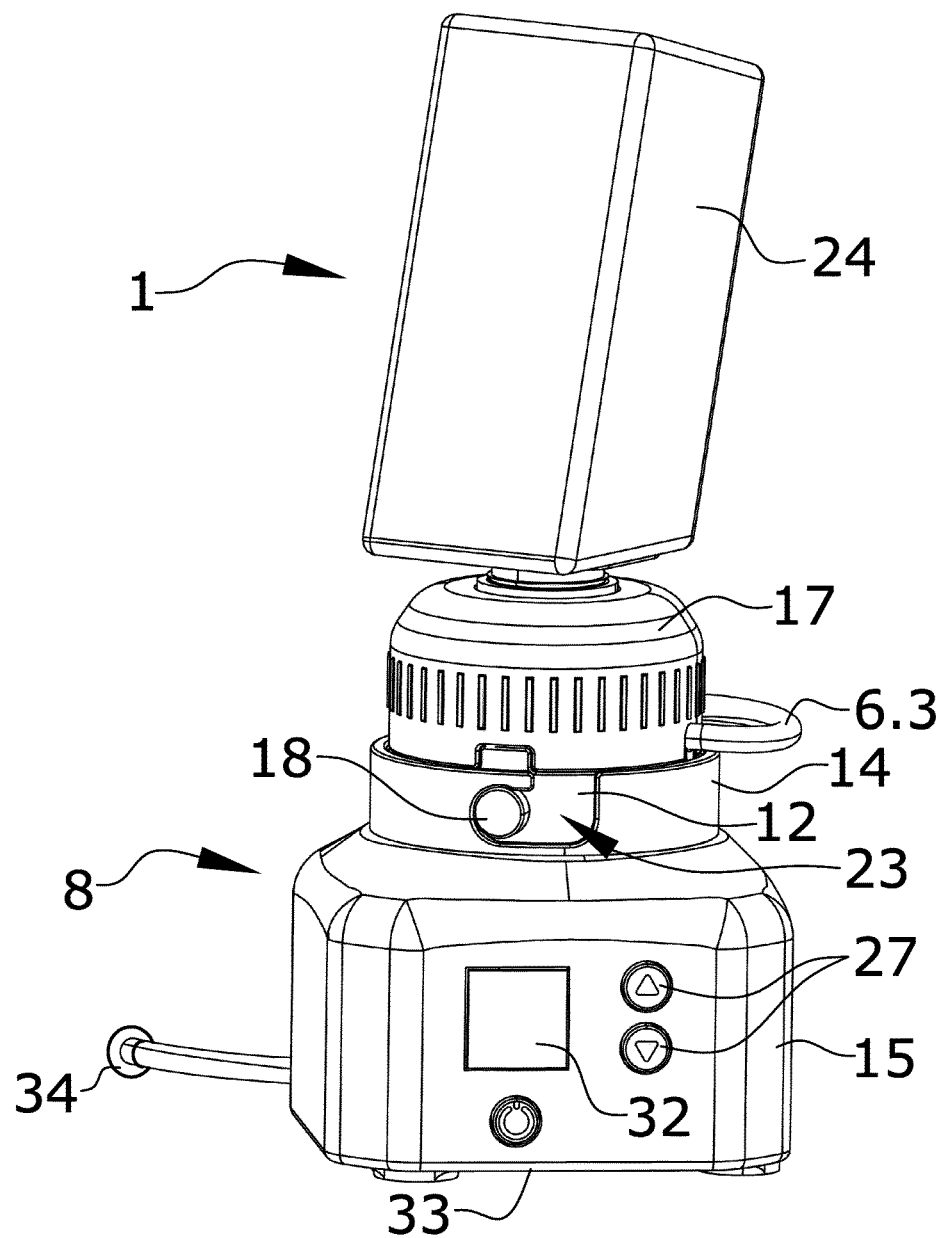
FIGS. 2A-2B show two perspective views, respectively, of the system of FIG. 1.
Figure 2B:
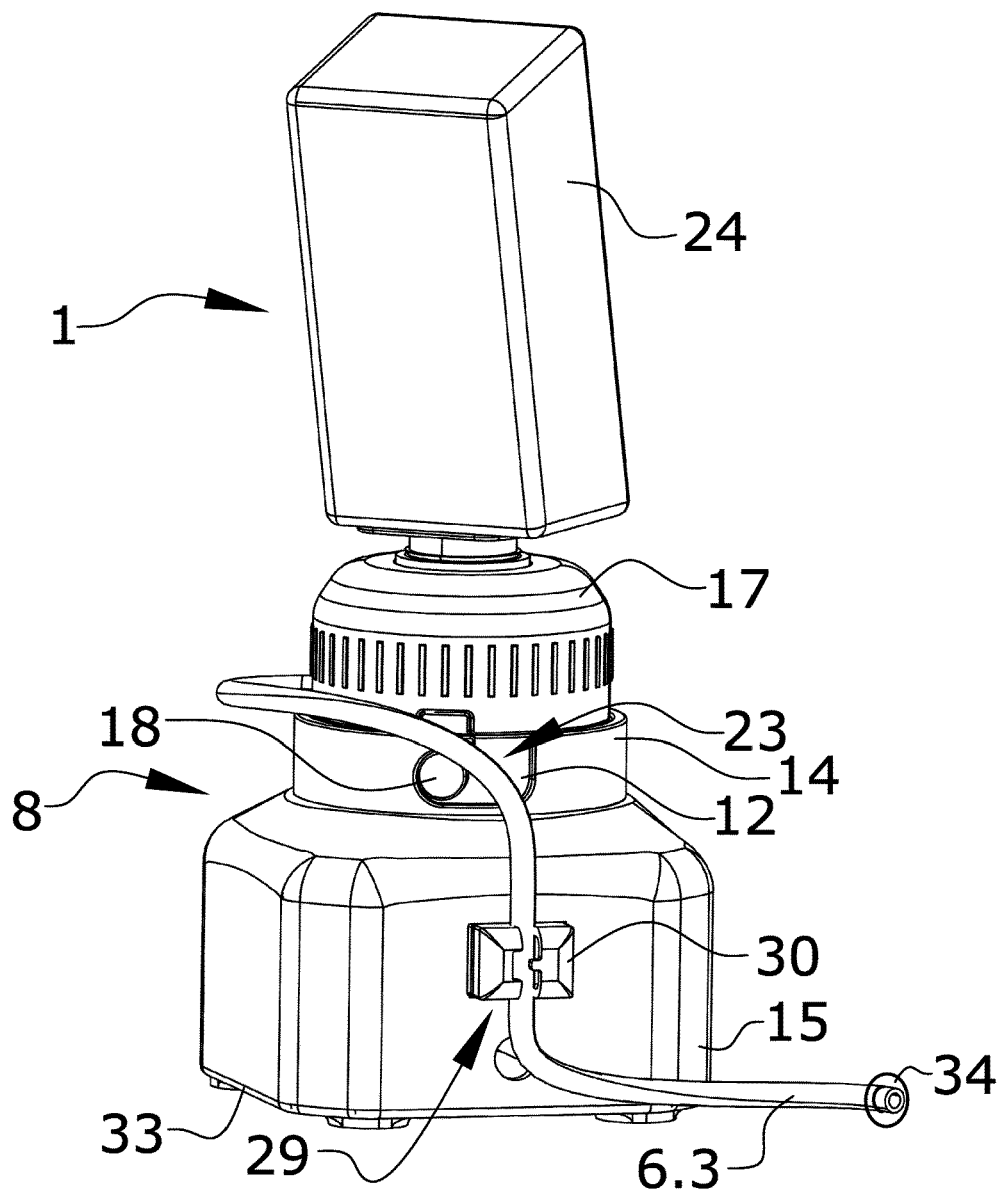

FIGS. 2A-2B show two side perspective views of the drive system coupled to a container (24) according to the embodiment of FIG. 1. Both drawings show how the cap (1) comprises a casing (17) protecting the inner components thereof from the outside, and it also comprises a third conduit (6.3), in this embodiment a flexible conduit, arranged on the outside of the cap (1). The drive head (8) shown in these drawings comprises the first casing segment (14) having a groove (23) receiving a protrusion (18) projecting radially from a second frame segment (12) of the cap (1). In this manner and as shown in FIG. 1, the cap (1) according to the first embodiment is coupled/fixed to the drive head (8) by means of the insertion of the protrusion (18) in the groove (23) of the drive head (8).

Both FIGS. 2A-2B show an enteral feeding container (24) coupled in the upper part of the feeding cap (1). Furthermore, the way in which the third conduit (6.3) is connected to one end to the feeding cap (1) and at the opposite end to a connector (34) can be seen. In a particular example, the third conduit (6.3) is a transparent flexible tube. In a particular example, the connector (34) is an Enfit connector.

In particular, FIGS. 1 and 2A show the drive head (8) according to the first embodiment comprising a display (32) suitable for showing the characteristics of the product being supplied. This display (32) is located in the second casing segment (15) of the drive head (8). Furthermore, this drive head (8) comprises ON/OFF means (27) in the form of ON/OFF buttons. These ON/OFF means (27) allow turning the operation of the operating means of the drive head (8) ON or OFF (not shown in these drawings).

FIG. 2B particularly shows how the third conduit (6.3) of the cap (1) according to this first embodiment is fixed to an optoelectric sensor (29) by means of holding means (30) arranged in the second casing segment (15) of the drive head (8). This optoelectric sensor (29) allows identifying if the product is circulating through the inside of the flexible conduit, particularly through the inside of the third conduit (6.3).

Figure 3:
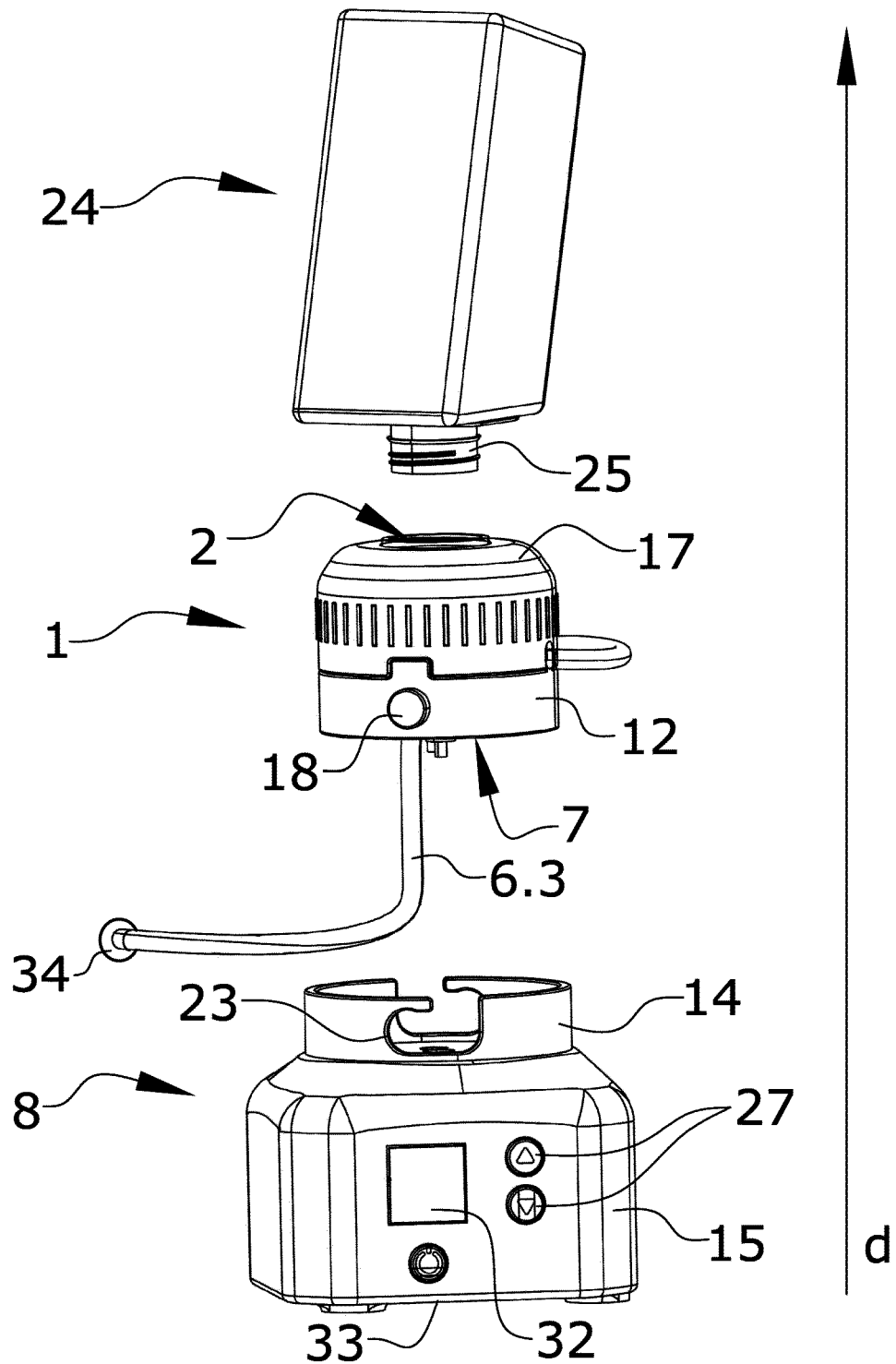
FIG. 3 shows an exploded view of the drive head, the cap, and the container shown in FIG. 1.

FIG. 3 shows an exploded view of a container (24), a cap (1) according to the first embodiment, and a drive head (8), all corresponding to those shown in FIGS. 1 and 2A-2B. In particular, the way in which the container (24) comprises a neck (25) through which the container (24) is coupled to the cap (1) according to longitudinal direction d can be seen. In particular, the neck (25) comprises a thread suitable for attachment inside the first cavity (2) of the feeding cap (1) by threading.

The drive head (8) comprises a plurality of rollers (10) (shown in FIGS. 5 and 8) projecting from the first casing segment (14) of this head, such that when the cap (1) is coupled to the drive head (8) the rollers (10) are housed inside the second cavity (7) of the cap (1).

The cap (1) according to this first embodiment is configured for being coupled with the drive head (8) by means of the insertion of the protrusion (18) projecting from the second frame segment (12) of the cap (1) in the groove (23) arranged in the first casing segment (14) of the head (8).

Figure 4:
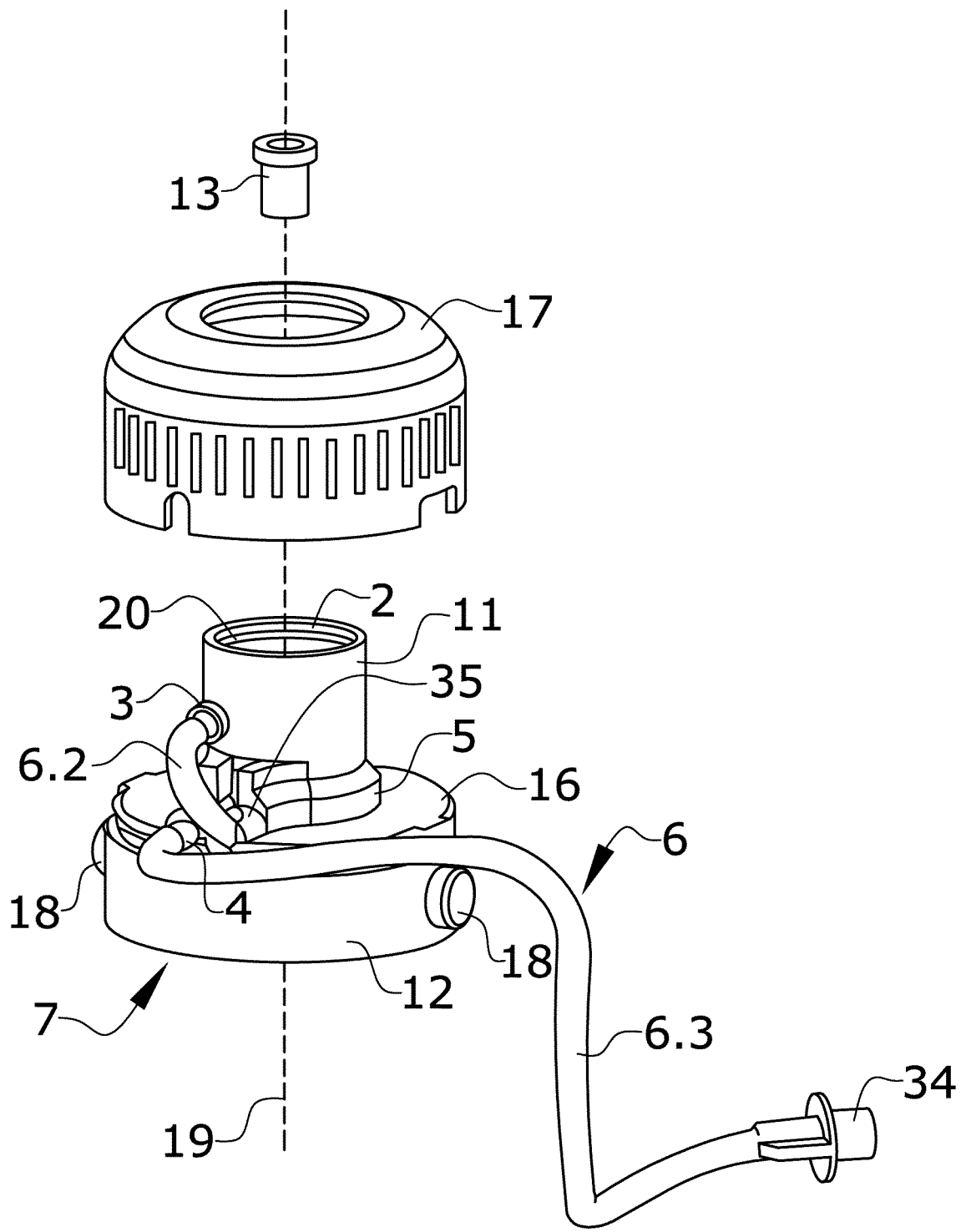
FIG. 4 shows an exploded perspective view of the feeding cap according to a particular example of the present disclosure.

FIG. 4 shows an exploded view of the cap (1) according to the first embodiment of the first inventive aspect, wherein the components shown in exploded view are arranged along a central axis (19) parallel to longitudinal direction d. The cap (1) comprises a first frame segment (11) defining a first open cavity (2) for receiving therein the product to be supplied. This first cavity (2) comprises coupling means suitable for allowing the coupling of the neck (25) of a container (24) with the cap (1). In a particular example, the coupling means (20) between the neck (25) of the container (24) and the cap (1) is a thread surface arranged in the inner walls of the first cavity (2) of the cap (1) as shown, for example, in FIG. 4. This first cavity (2) defines a cylindrical opening around the central axis (19).

The cap (1) further comprises a second frame segment (12) and a disc (16) which together define the second open cavity (7) defining a cylindrical opening around the central axis (19), such that the opening of the first cavity (2) is arranged in opposition to the opening of the second cavity (7). The cap (1) further comprises a support seating (5) structure suitable for housing therein a first flexible conduit segment (6.1) (shown in the section view of FIG. 6). Furthermore, the cap (1) has a connection adaptor (35) that connects on one hand with a second conduit (6.2), in this embodiment a flexible conduit, which in turn connects with a first outlet port (3) arranged in the first cavity (2), and on the other hand, the adaptor (35) connects with the third conduit (6.3) through a second outlet port (4) arranged in the second cavity (7). In this manner, the conduit (6) is formed by a first flexible conduit segment (6.1), a second conduit segment (6.2), and a third conduit segment (6.3), all of them being in fluid connection through the different connections that have been described.

The second frame segment (12) of the cap (1) comprises two protrusions (18) projecting radially outwards from this second frame segment (12). These protrusions (18) are sized to enable fitting in the grooves (23) of the drive head (8) (as shown in FIG. 3) configuring the bayonet lock according to this embodiment.

FIG. 4 further shows a casing (17) according to the first embodiment suitable for housing therein the first frame segment (11), the support seating (5), and the second conduit (6.2). This casing (17) comprises in its upper part a perforation matching the opening of the first cavity (2) to allow the coupling of the neck (25) of a container (24) inside this first cavity (2).

Furthermore, the cap (1) comprises filtering means (13) which facilitate the passage of air between the second cavity (7) and the first cavity (2). In a particular example, the filtering means (13) comprise a membrane configured for allowing the passage of air, preventing the passage of fluid/product. Furthermore, this membrane is configured for preventing the passage of particles such that it advantageously assures the sealing of the product housed inside the first cavity (2), i.e., the product is prevented from being contaminated.

In a particular example, the attachment between the second conduit segment (6.2) and the first outlet port (3), as well as the connection between the third conduit (6.3) and the connector (34), is carried out by means of a sealing adhesive.

Figure 5:
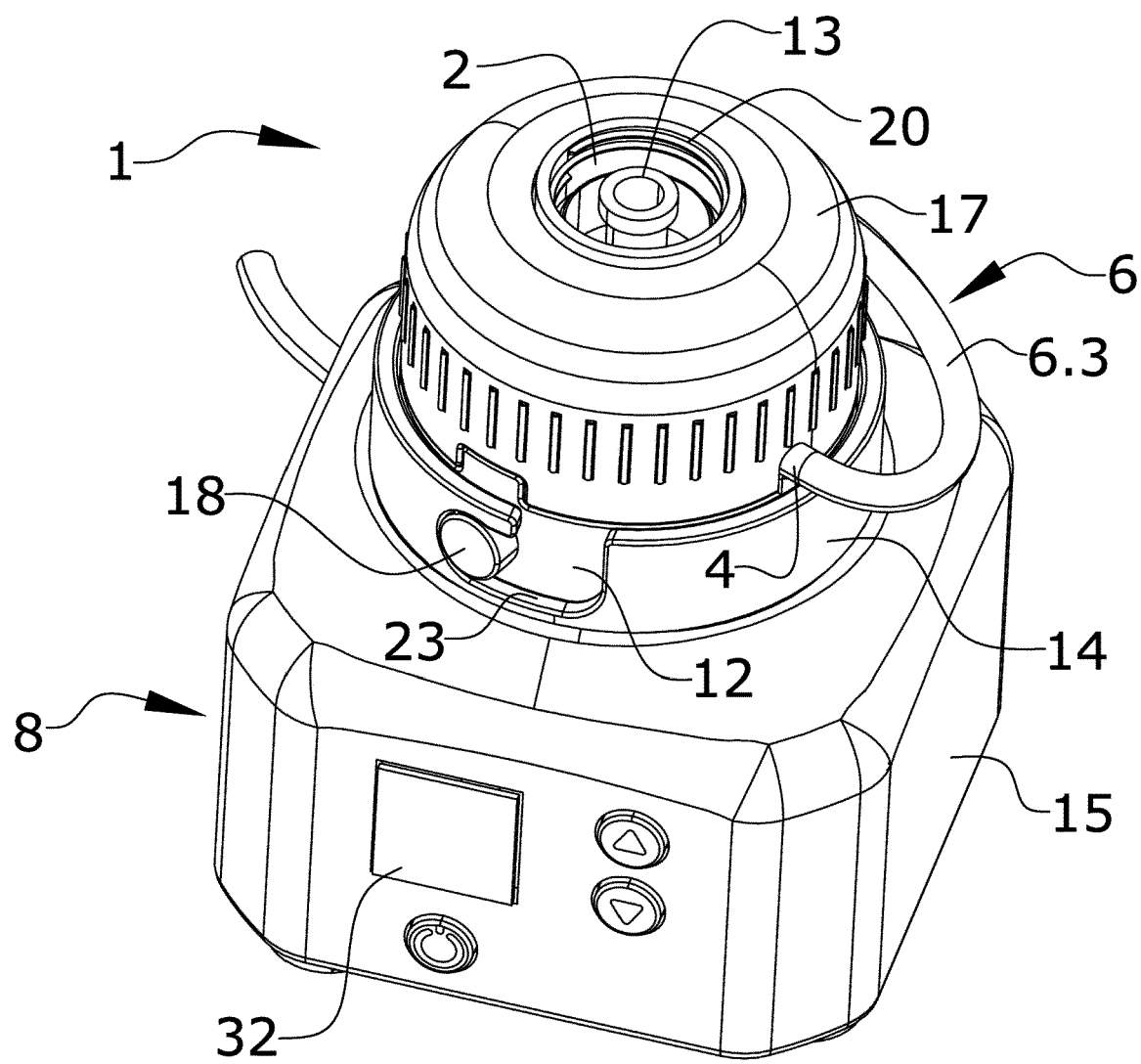
FIG. 5 shows a perspective view of the drive head according to a particular embodiment of the present disclosure.

FIG. 5 shows a top perspective view of the drive system according to the first embodiment of the third inventive aspect of the disclosure. In particular, the cap (1) is seen coupled to the drive head (8) through the insertion of the protrusion (18) of the second frame segment (12) of the cap (1) in the groove (23) of the first casing segment (14) of the head (8).

In particular, FIG. 5 shows how the upper opening of the casing (17) matches the opening of the first cavity (2). This first cavity (2) comprises thread-type coupling means (20) for being coupled to the neck (25) of a container (24). When the cap (1) is coupled to the neck (25) of the container (24), the product contained in said container (24) is poured into the first cavity (2) of the cap (1). Furthermore, in this drawing the way in which the filtering means (13) are arranged in the cap (1) can be seen, such that they come into contact with the products coming from the container when the cap (1) is coupled to said container through its neck.

FIG. 5 shows the second outlet port (4) arranged in the second cavity (7) of the cap (1), such that the third conduit segment (6.3) connects at one end with the second outlet port (4).

Figure 6:
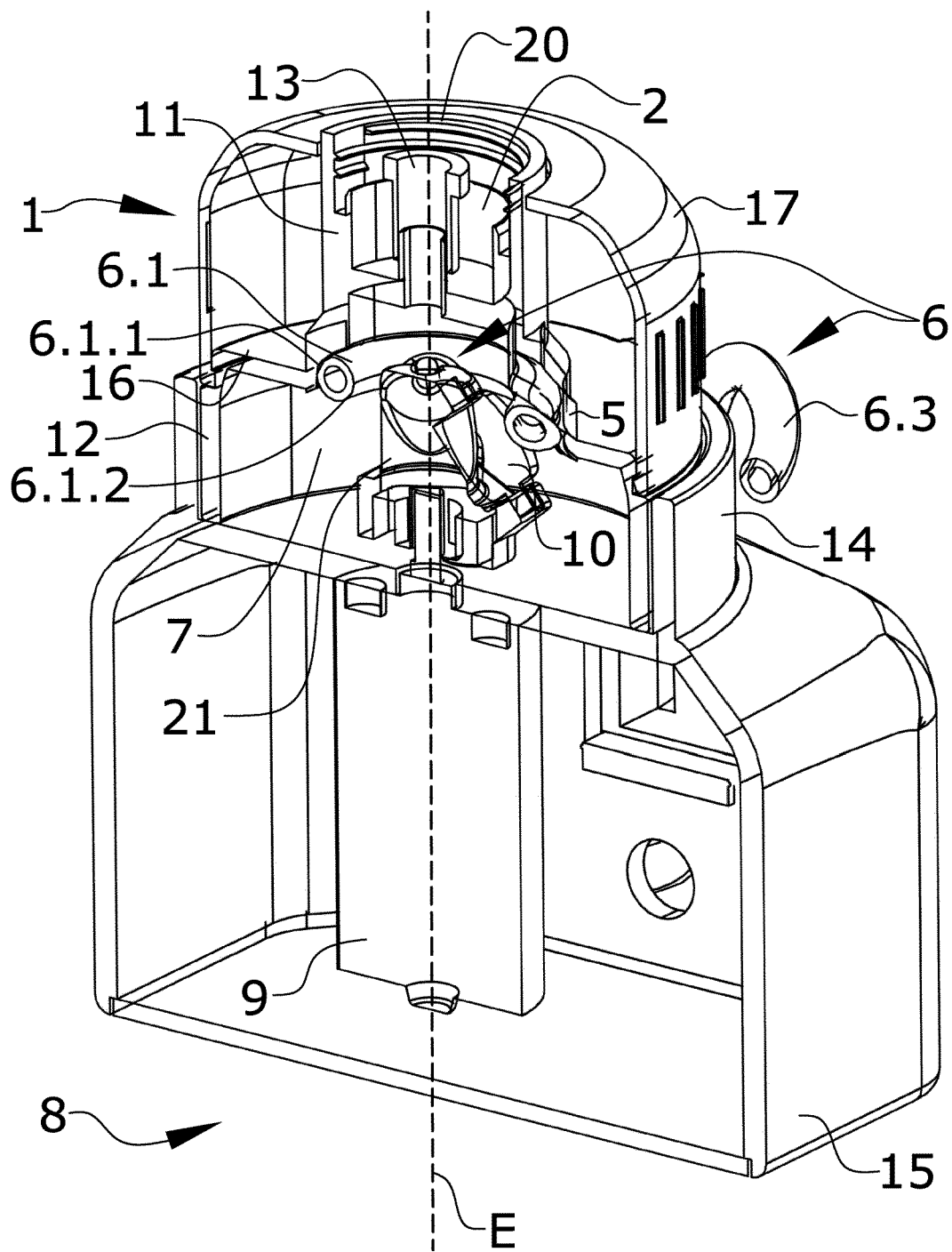
FIG. 6 shows a perspective view of a section of the drive head of FIG. 5.

FIG. 6 shows an inner section of the drive system shown in FIG. 5. In particular, the way in which the filtering means (13) connect the second cavity (7) with the first cavity (2) of the cap (1) can be seen. Furthermore, the way in which the casing (17) houses therein the first frame segment (11) and is supported on the peripheral area of the disc (16) can be seen. More particularly, the casing (17) can be coupled to the second frame segment (12) through clipping with the peripheral area of the disc (16). Furthermore, the way in which the first flexible conduit segment (6.1) of the conduit (6) is housed in or supported on the support seating (5) can be seen.

The way in which the drive head (8) comprises a first frame segment (14) defining a cylindrical sector housing a roller frame (21) and the plurality of rollers (10) can furthermore be seen in FIG. 6. In turn, the drive head (8) comprises a second casing segment (15) defining a closed cavity in which the operating means (9) are housed.

When the cap (1) is in the operating mode with the drive head (8), the operating means (9) of this head (8) operate the rotation or turning of the roller frame (21) around the axis of rotation E, such that this rotation is transmitted to the rollers (10), and these rollers (10) rotate, pressing the first flexible conduit segment (6.1) which is supported on the support seating (5) of the feeding cap (1), thereby pumping the fluid flowing through the inside of the first flexible conduit segment (6.1) to a third flexible conduit (6.3).

Figure 7:
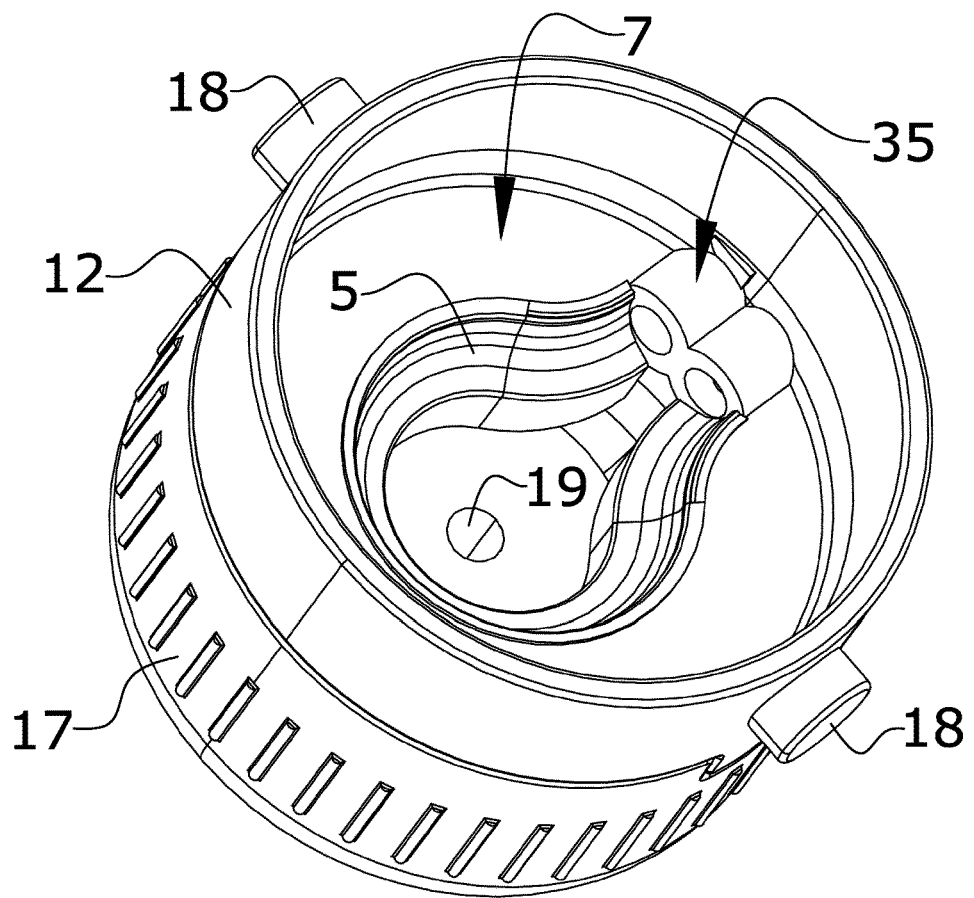
FIG. 7 shows a bottom perspective view of the feeding cap according to a particular embodiment of the present disclosure.

FIG. 7 shows a bottom view of the cap (1) according to the first embodiment. In particular, the inside of the second cavity (7) and the support seating (5) can be seen. This support seating (5) defines a surface segment in the form of a band the directrix of which extends in a circle around a central axis (19) (not shown in this drawing) and in a plane transverse to longitudinal direction d. The section of this surface of the support seating (5) according to a plane going through the central axis (19) is an arc-shaped segment. In particular, the arc-shaped segment has normal direction corresponding to the surface of the support seating (5) that is oblique and oriented towards the outside of this second cavity (7).

The way in which the cap (1) comprises two protrusions (18) projecting from the second frame segment (12) towards the outside of the second cavity (7) can furthermore be seen in FIG. 7.

The feeding cap (1) in turn comprises a connection adaptor (35) arranged at the ends of the support seating (5) such that each connection of the connection adaptors (35) matches each end of the circular band defining the support seating (5).

Figure 8:
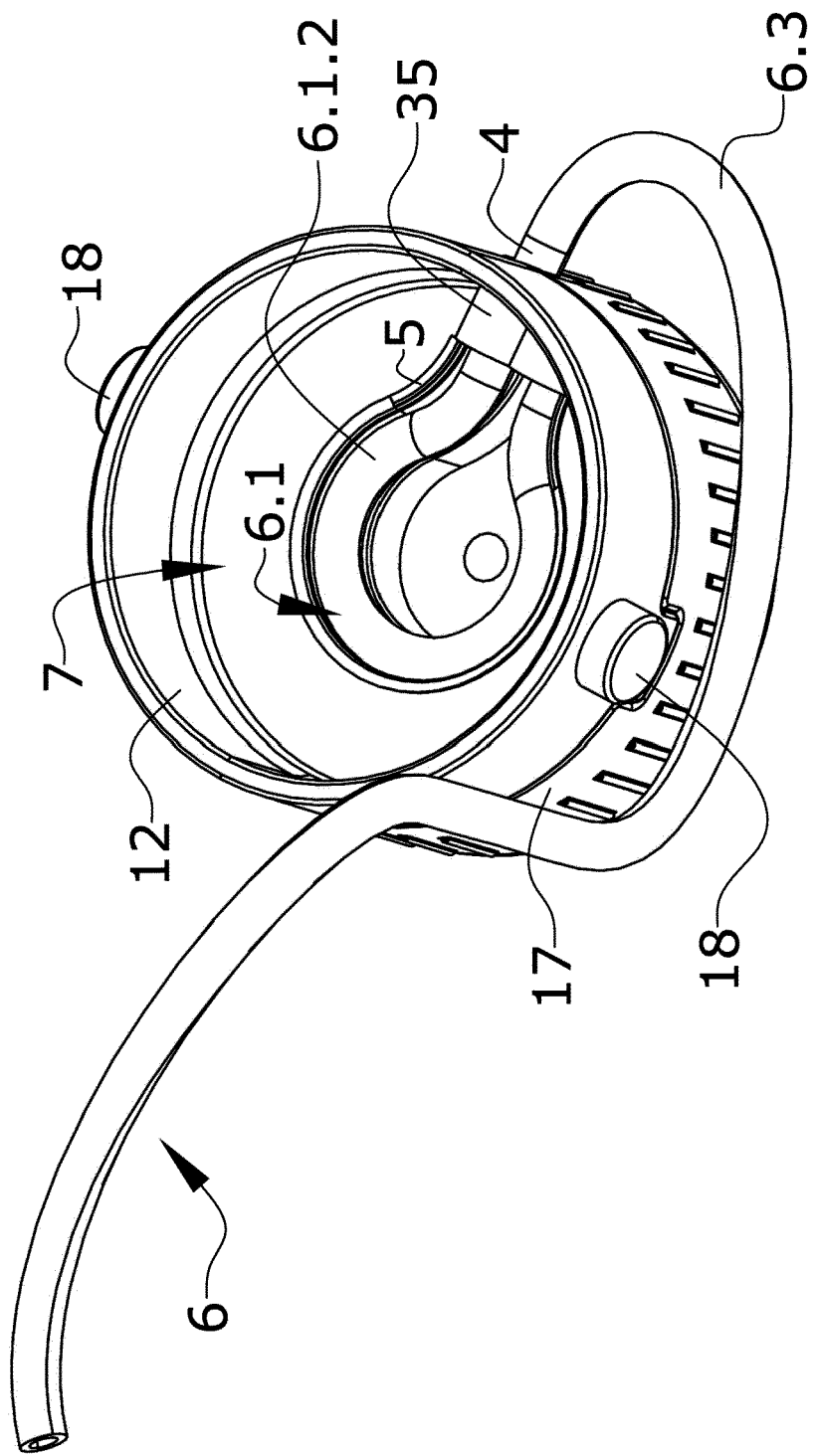
FIG. 8 shows a bottom perspective view of the feeding cap according to a particular embodiment of the present disclosure.

FIG. 8 shows a bottom view of a cap (1) comprising the same features as the cap (1) defined in FIG. 7. In particular, FIG. 8 shows the arrangement of a first flexible conduit segment (6.1) and a third conduit (6.3). The first flexible conduit segment (6.1) is housed in or supported on the support seating (5) and connected at its two ends with the connections of the connection adaptors (35). In turn, one of the connections of the connection adaptor (35) connects with the second outlet port (4) to which the third conduit (6.3) arranged on the outside of the feeding cap (1) is connected. The first flexible conduit segment (6.1) shown in FIG. 8 comprises a first region (6.1.1) which is supported on the support seating (5) and a second region (6.1.2) which is arranged in opposition to the first region (6.1.1) in the first flexible conduit segment (6.1) to allow rotary rollers (10) of the drive head (8) (as shown in FIG. 5) to press on this second region (6.1.2), such that when the cap (1) is in the operating mode with the drive head (8) the fluid contained inside the flexible conduit (6) is driven by the action of the rollers (10).

In a particular example, the radius of curvature of the arc-shaped segment of the section of the surface of the support seating (5) is greater than the radius of curvature of the cross section of the flexible conduit (6).

Figure 9:
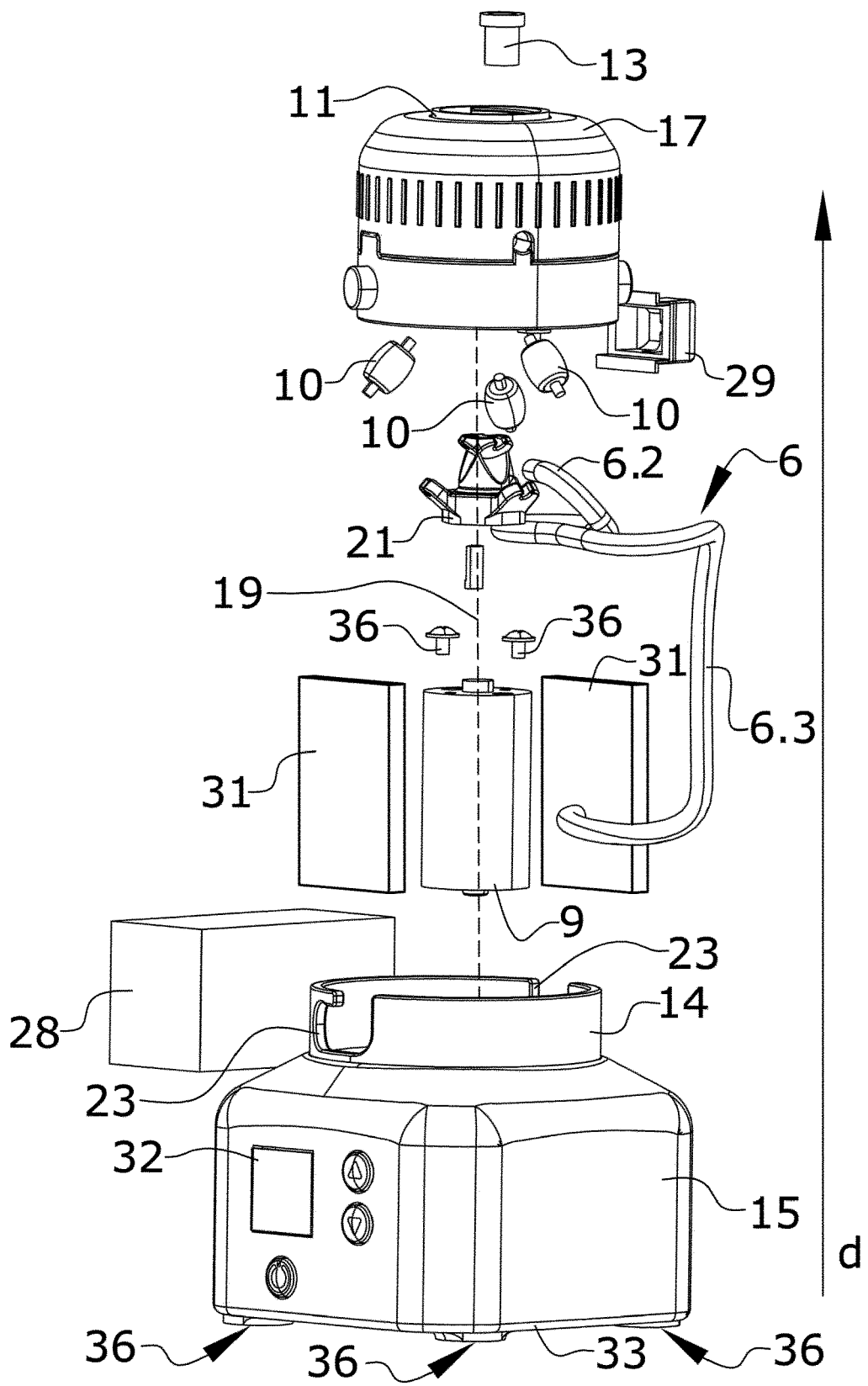
FIG. 9 shows an exploded perspective view of the drive head according to a particular embodiment of the present disclosure.

FIG. 9 shows an exploded view of the components forming a drive head (8) according to the first embodiment. This head (8) comprises a casing formed by two casing segments (14, 15) extending according to a longitudinal direction d. The first casing segment (14) is configured in the form of a cylindrical sector for housing the plurality of rollers (10), this cylindrical sector defining an open cavity suitable for receiving the cap (1). The first casing segment (14) is configured for receiving the cap (1) according to a length direction d. Furthermore, this first casing segment (14) comprises two grooves (23) each configured for receiving a protrusion (18) of the cap (1), thereby defining a fixing system which facilitates the coupling of the cap (1) with the drive head (8). There is housed in this first casing segment (14) the roller frame (21) on which there are arranged and fixed the rollers (10) configured for rotating around the axis of rotation E. The roller frame (21) is fixed to the drive head (8), particularly in the cavity defined by the first casing segment (14), by means of a pair of screws (36). In particular, FIG. 9 shows the head (8) with three rollers (10).

The drive head (8) further comprises a second casing segment (15) configured in the form of a closed cavity housing therein the operating means (9). In particular, this cavity defining the second casing segment (15) comprises a base (33) which closes this cavity by means of a plurality of screws (36). In this particular example, an electronic system

(31) and a battery (28) are furthermore housed inside the second casing segment (15). This electronic system (31) responsible for regulating the turning ON/OFF of the operating means (9), as well as the infusion speed of the product to be supplied to the patient.

In a particular example (not shown in the drawings), the drive head (8) comprises a barcode or QR code reader which facilitates the traceability of the nutritional feeding of the patient in question, such that the patient's data, the feeding used, and the use of the device are recorded in a database accessible by nutritionists. This data can be readily downloaded by means of a cable or a Bluetooth unit connected to an external smartphone-type device.

The drive head (8) comprises at the same time an optical sensor for reading the blood pressure of the patient, and electrodes which allow analyzing body composition by means of the electrical bioimpedance technique.

These sensors provide information about highly relevant biomedical parameters in relation to the objectives of the nutritional product supplied, such as bone mass, fat mass, muscle mass, risk of dehydration, and blood pressure. This information is likewise transferred to the database accessible by nutritionists. In this manner, the device is configured as a complete system for delivering nutrition and tracking patient nutritional status.

An obvious example would be the case of a patient at risk of losing muscle mass (sarcopenia). The enteral feeding for said patient would focus on optimizing protein (leucine) and carotenoid ingestion; the device will not only facilitate supply, but will also allow knowing the degree of compliance to the diet (as a result of the usage record), and the effectiveness thereof (by means of continuously tracking skeletal muscle mass).

Figure 10:
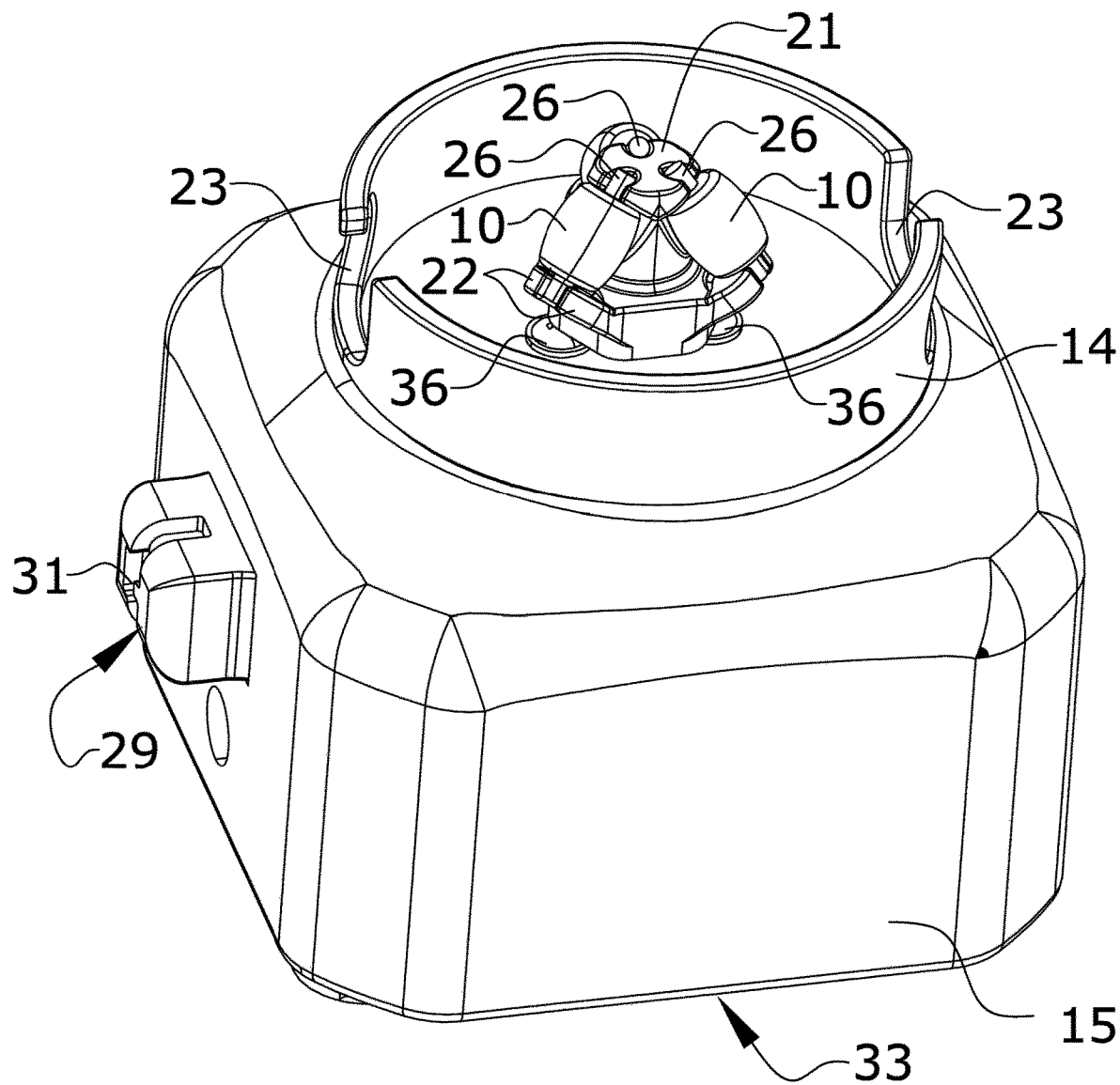
FIG. 10 shows a perspective view of the drive head according to a particular embodiment of the present disclosure.

FIG. 10 shows an exploded perspective view of the drive head (8) shown in an exploded view in FIG. 9. The way in which the roller frame (21) is fixed to the second casing segment (15) inside the cavity defining the first casing segment (14) by means of screws (36) can be seen. Furthermore, the way in which the optoelectric sensor (29) is arranged together with the holding means (31) on a side of the second casing segment (15) of the head on the outside thereof can be seen.

Figure 11:
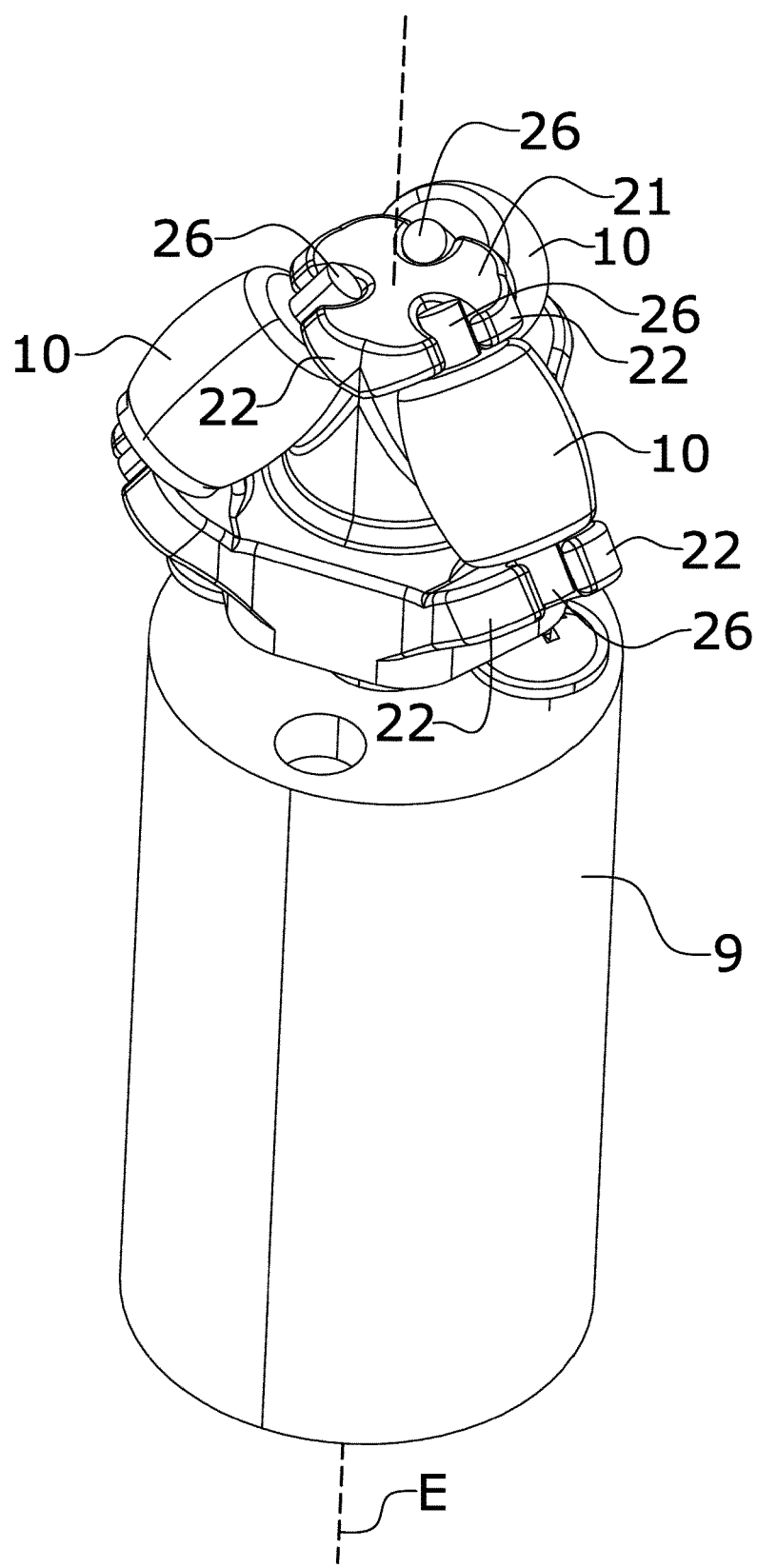
FIG. 11 shows a perspective view of the operating means of the drive head according to a particular embodiment of the present disclosure.

In a particular example, the optoelectronic sensor (29) is configured for detecting whether product or air circulates through the inside of the conduit (6) of the cap (1), such that when the drive head (8) is in the operating mode with the cap (1) and the optoelectronic sensor (29) detects that air circulates through the inside of the conduit (6) of the cap (1), rotation of the rollers (10) is stopped. This is achieved through the electronic system (31) of the drive head (8) (as shown in FIG. 9). FIG. 11 shows in detail the operating means (9) attached to the roller frame (21) of the drive head (8) shown in FIGS. 9-10. In particular, this drawing shows three rotary rollers (10) radially distributed around an axis of rotation E, the rotational or turning movement of which around this axis of rotation E is due to the operation of the operating means (9).

The rollers (10) shown in FIG. 11 are arranged with their oblique shafts (26) converging in the axis of rotation E, such that by being fixed to the roller frame (21) the oblique shafts (26) are all configured for rotating around the axis of rotation E. In particular, each oblique shaft (26) is fixed to the roller frame (21) by means of two clipping clamps (22) arranged according to longitudinal direction d, with one clipping clamp (22) being located closer to the axis of rotation E than the other opposite clipping clamp (22) such that the roller (10) is arranged in an oblique position between both clipping clamps (22).

Figure 12:
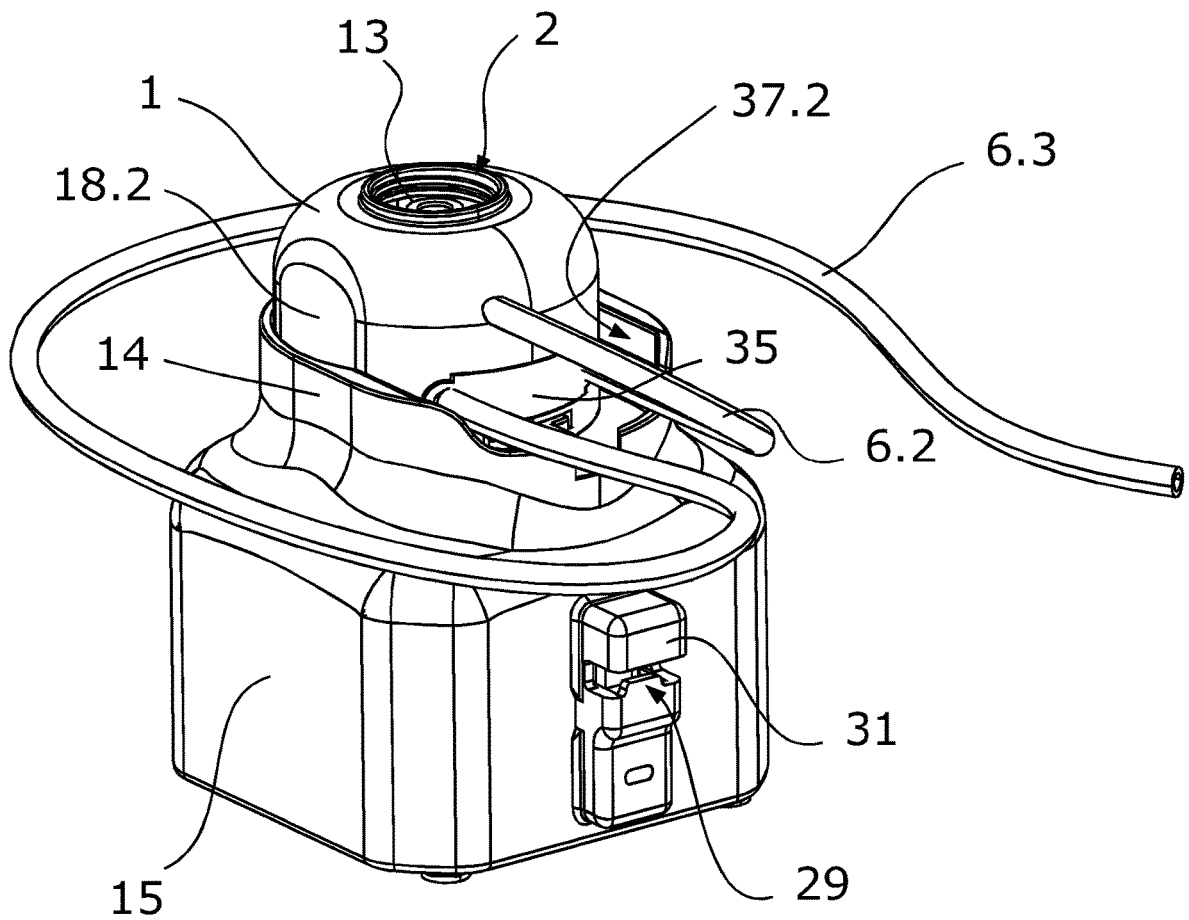
FIG. 12 shows a perspective view of a second embodiment of the third aspect of the disclosure wherein a linear bayonet locking is used.

FIG. 12 shows a perspective view of a second embodiment of the third aspect of the disclosure wherein a linear bayonet locking is used.

This second embodiment shares most of the features and elements already disclosed in the first embodiment; therefore, only those elements being different will be disclosed as the former description applies mutatis mutandis for common elements of this embodiment.

As described above, in the first embodiment, the cap (1) is locked using a bayonet locking wherein the cap (1) is inserted into the first casing element (14) according to the longitudinal direction d and further rotated around the same direction in order to lock the cap (1) in the first casing segment (14) of the drive head (8).

During the insertion movement the first flexible conduit segment (6.1) housed in the cap (1) is compressed as the final axial movement is the position where the oblique rollers (10) are pressing against said first flexible conduit segment (6.1).

In this final axial position of the cap (1) and also after rotating the cap (1) for locking it, the first flexible conduit segment (6.1) is pressed by the set of rollers (10) according to the oblique direction against the support seating (5) generating some shear stresses.

The second embodiment of the disclosure combines a different bayonet locking, particularly a linear bayonet locking, and an arrangement of the set of rollers (10) wherein said rollers (10) have their rotational axis parallel to the axis of rotation of the roller frame (21).

According to this second embodiment, FIG. 12 shows the drive head (8) wherein the first casing segment has an elongated shape because it houses the cap (1) in two different positions: and insertion position and a final locking position.

Figure 13A:
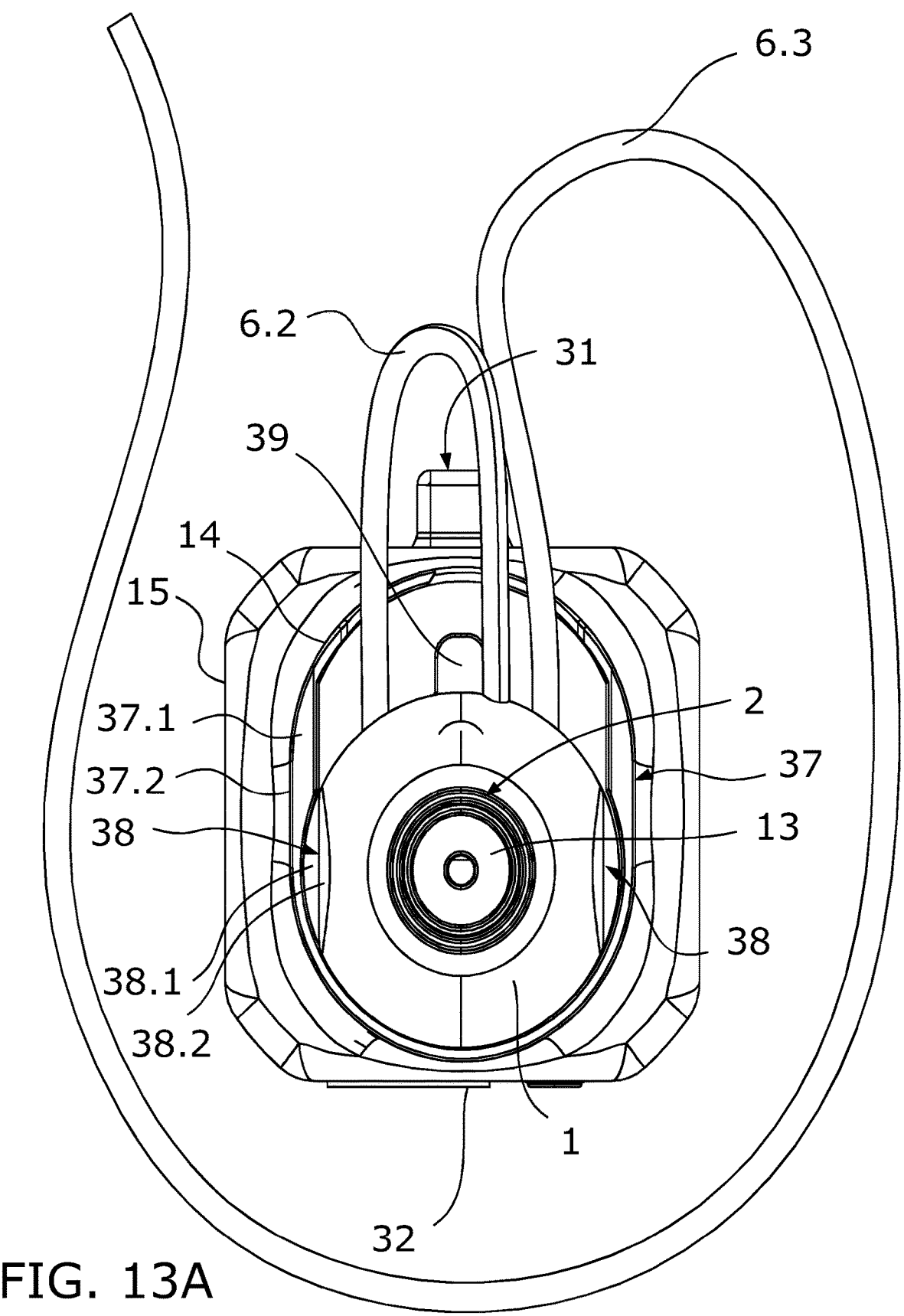
FIG. 13A shows a top view of the second embodiment wherein the cap is in a first insertion position and, FIG. 13B shows also a top view of the same embodiment wherein the cap is in a second final locking position.

FIG. 12 shows the cap (1) after being inserted and housed into the first casing (14) in the first insertion position by an axial movement. This first insertion position is also shown in FIG. 13A wherein the top view of FIGS. 13A and 13B allows to view the elongated shape of the first casing segment (14) and the linear guiding means of the driving head (37) cooperating with the linear guiding means of the cap (38).

Both linear guiding means (37, 38) allows the cap (1) to move between the first insertion position and a second final locking position according to a linear movement perpendicular to the insertion direction; i.e. perpendicular to the longitudinal direction d.

Once the cap (1) has been moved to the second final locking position, a locking element locks the cap (1) avoiding said cap (1) to return to the first insertion position unless the locking element releases the cap (1). The locking element is preferably a clip retention element.

The linear guiding means (38) of the cap (1) comprises a portion of the cap (1) configured as a flat surface (38.1) and a further portion of the cap (1) configured as a planar wall (38.2).

The linear guiding means (37) of the driving head (8) comprises a plate (37.1) intended for retaining the cap (1) by resting against the flat surface (38.1) of the cap (1), and a planar wall (37.2) configuring a longitudinal channel in the inner space of the first casing segment (14) guiding the cap (1) in the movement between the first insertion position and a second final locking position. The edge of the plate (37.1) is straight and is configured to be an sliding surface for the flat surface (38.1) of the cap (1) preventing the cap (1) to rotate in the longitudinal direction d.

The plate (37.1) is intended to retain the cap (1) but it shows an arc shaped recess (37.3) configured to allow the entrance of the cap (1) during the insertion movement into the inner space of the first casing segment (14).

Figure 13B:
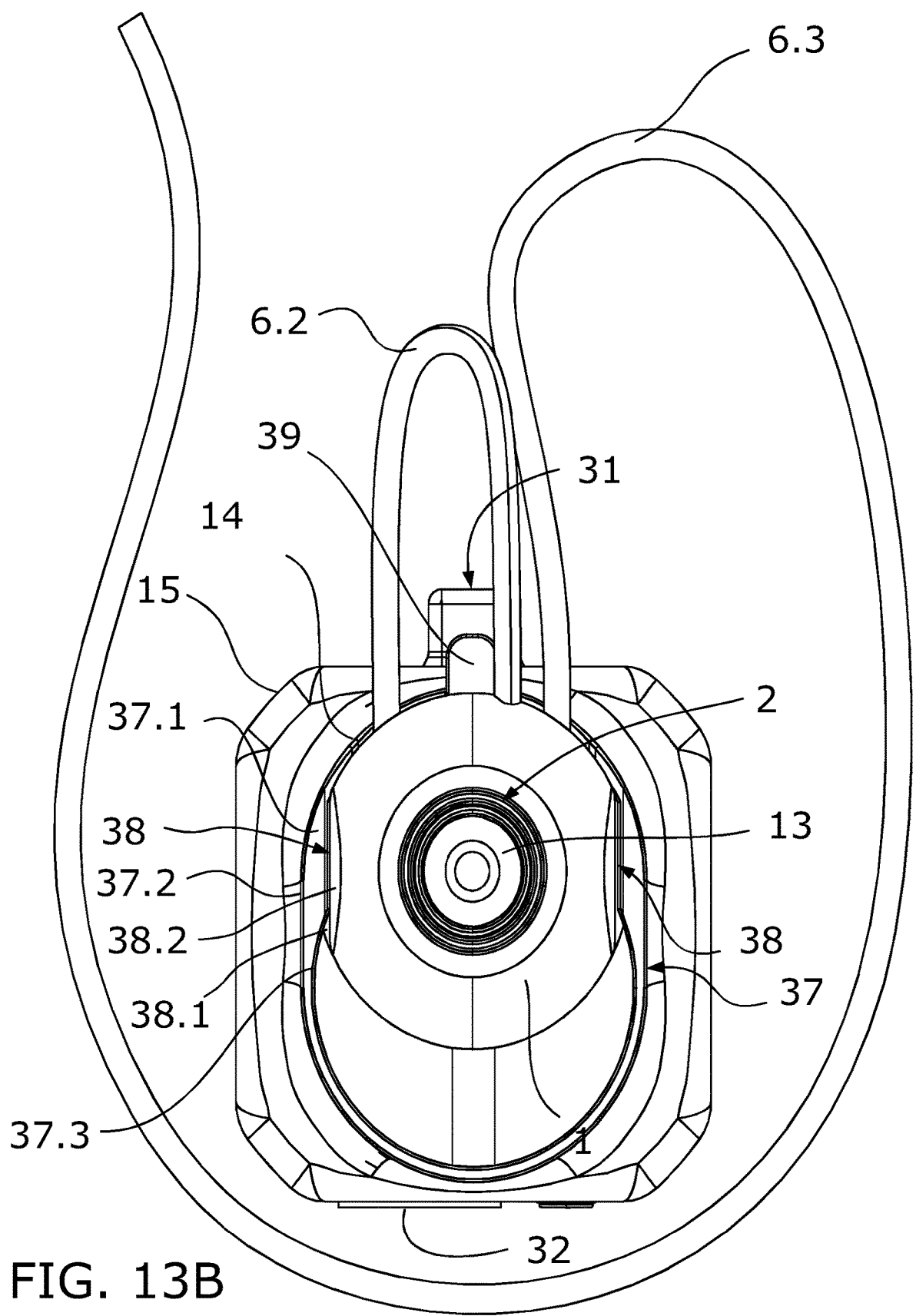

FIG. 13B shows the cap (1) once in the second final locking position allowing to shows in a more clear manner the arc shaped recess (37.3) configured to receive the cap (1) and the plate (37.1) resting on the flat surface (38.1) of the cap (1). In this final position, the locking element (39) is projected out of the inner space of the first frame segment (11) allowing an easy access for releasing the cap (1) again.

Figure 14:
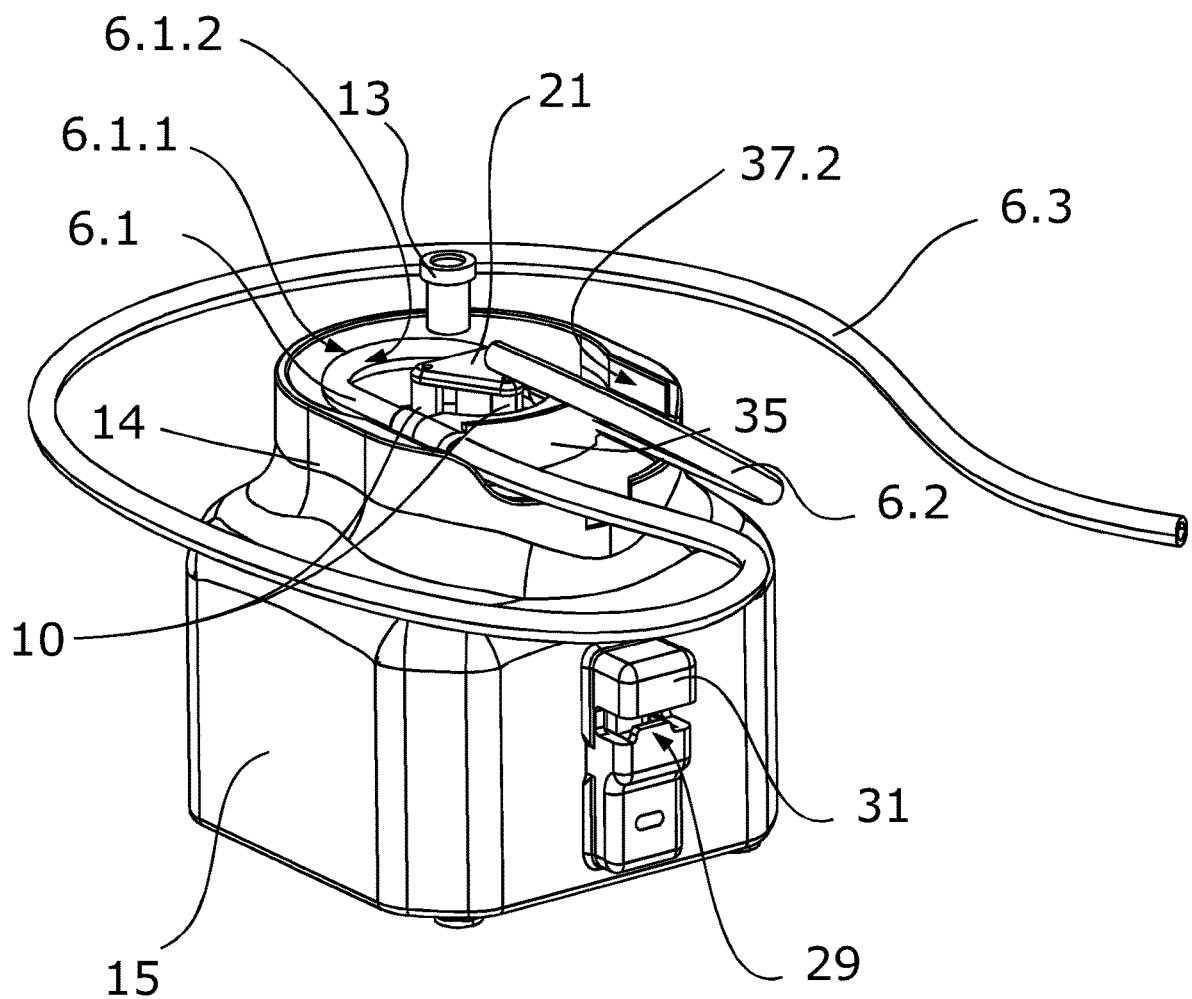
FIG. 14 shows a perspective view according to FIG. 12 wherein the cap has been removed in order to have visual access to the inner part where the roller frame drives the movement of the fluid over the first flexible conduit segment.

FIG. 14 shows a perspective view according to FIG. 12 wherein the cap (1) has been removed in order to have visual access to the inner part of the cap (1); that is, only the external surface of the cap (1) has been removed showing the first flexible conduit segment (6.1).

The first flexible conduit segment (6.1) is housed in the inner space of the second cavity of the cap (1). The cap (1) comprises a first frame segment (11) defining the first cavity (2) and, a second frame segment (12) defining the second cavity (7).

Figure 17:
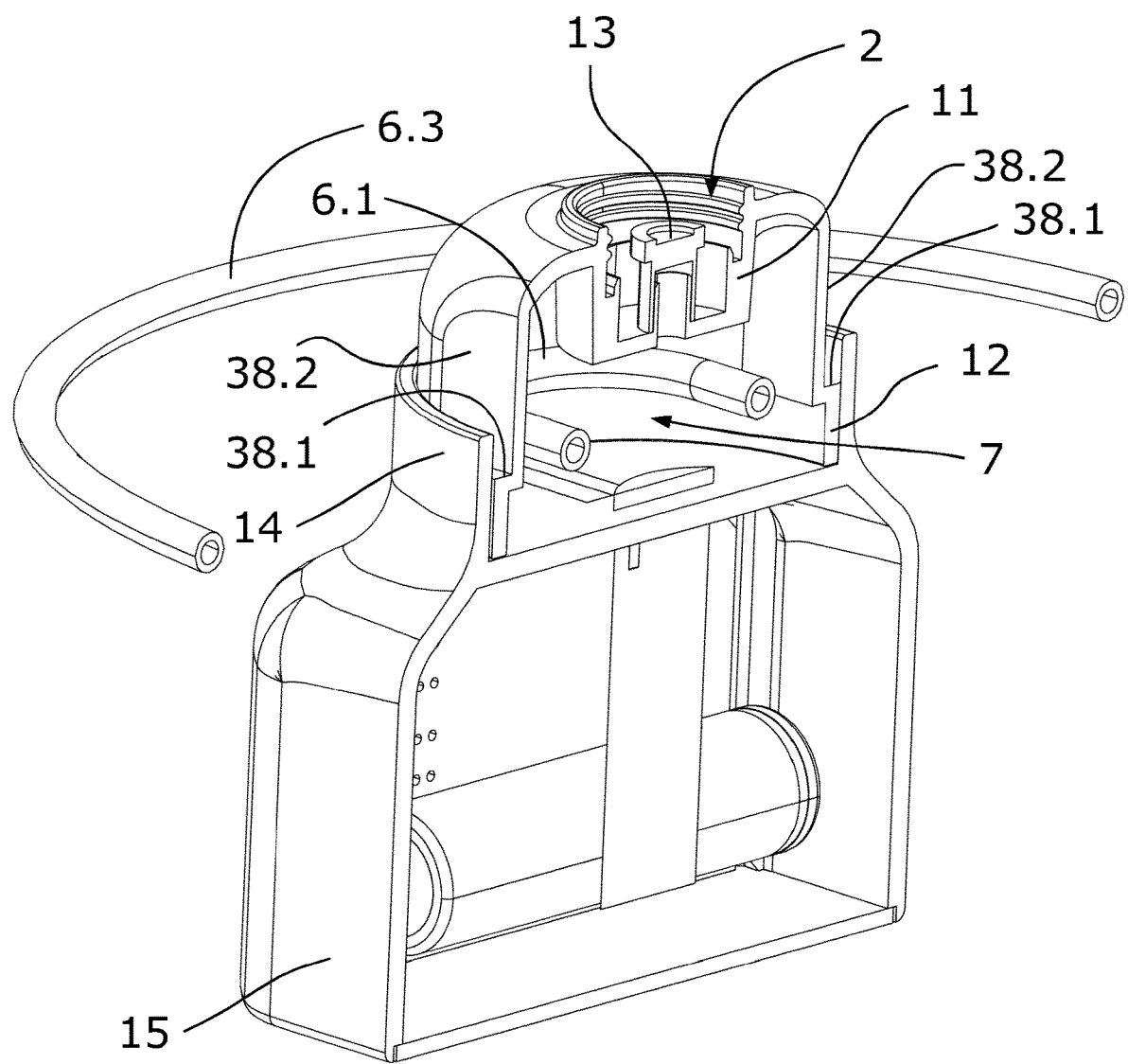
FIG. 17 shows a sectional view of the second embodiment in order to have view access to the inner space of the cap including the conduits.

In this embodiment, as it is shown in FIG. 17, the first flexible conduit segment (6.1) comprises a first region (6.1.1) which is resting on the cylindrical inner wall of the second frame segment (12) and a second region (6.1.2), in opposition to the first region (6.1.1), intended for being pressed by the set of rollers (10).

Figure 15:
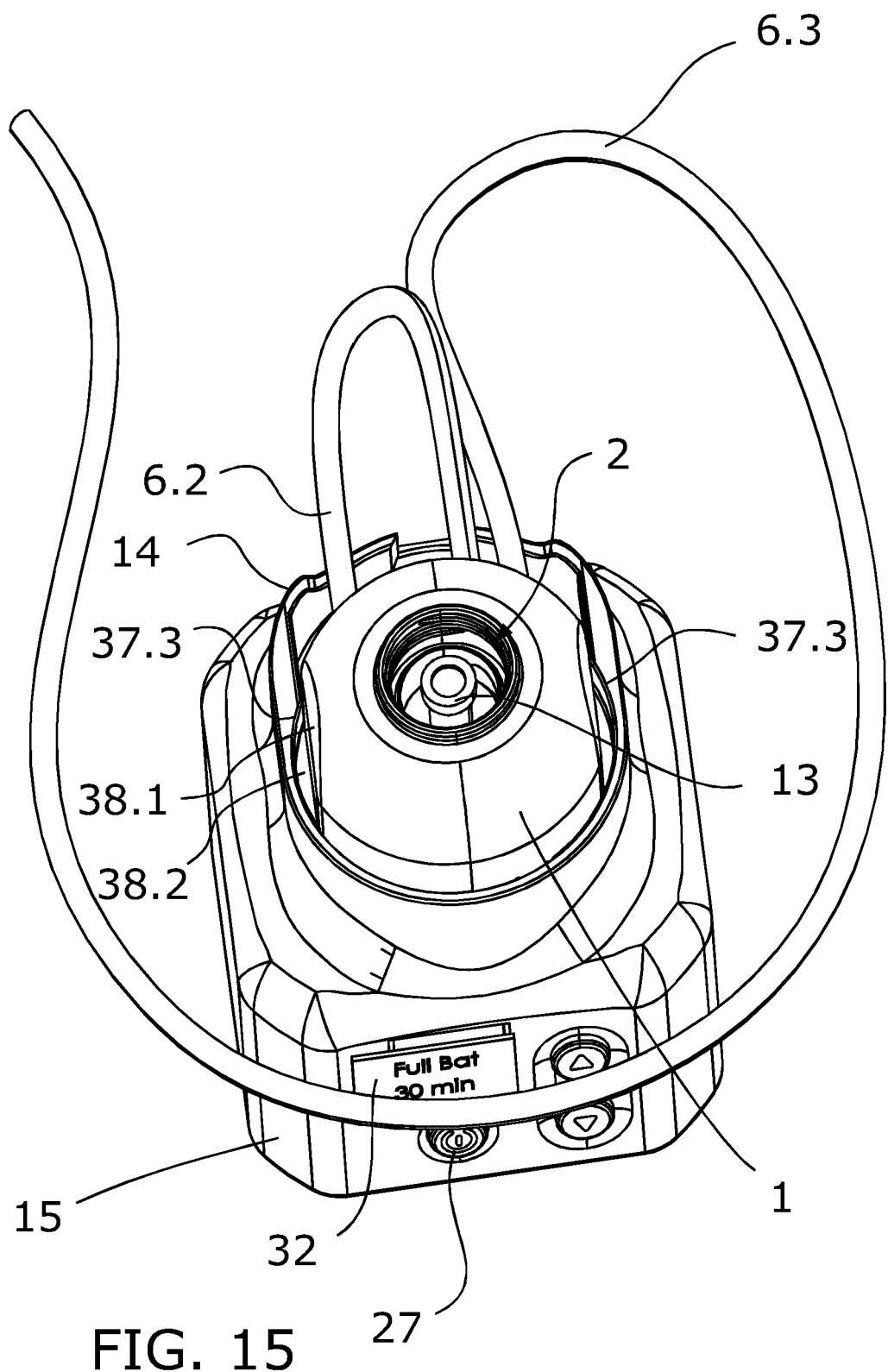
FIG. 15 shows an elevational view with the cap in an intermediate position between the first insertion position and the second final locking position.

When the cap (1) is inserted into the first casing segment (14) in the first insertion position, the first region (6.1.1) of the first flexible conduit segment (6.1) is spaced from the set of rollers (10). FIG. 15 shows an elevational view with the cap (1) in an intermediate position between the first insertion position and the second final locking position wherein according to this movement departing from the first insertion position, the first region (6.1.1) of the first flexible conduit segment (6.1) is approximated to the set of roller (10). At the second final locking position, the set of rollers (10) are pressing against the second region (6.1.2) of the first flexible conduit segment (6.1).

Figure 16:
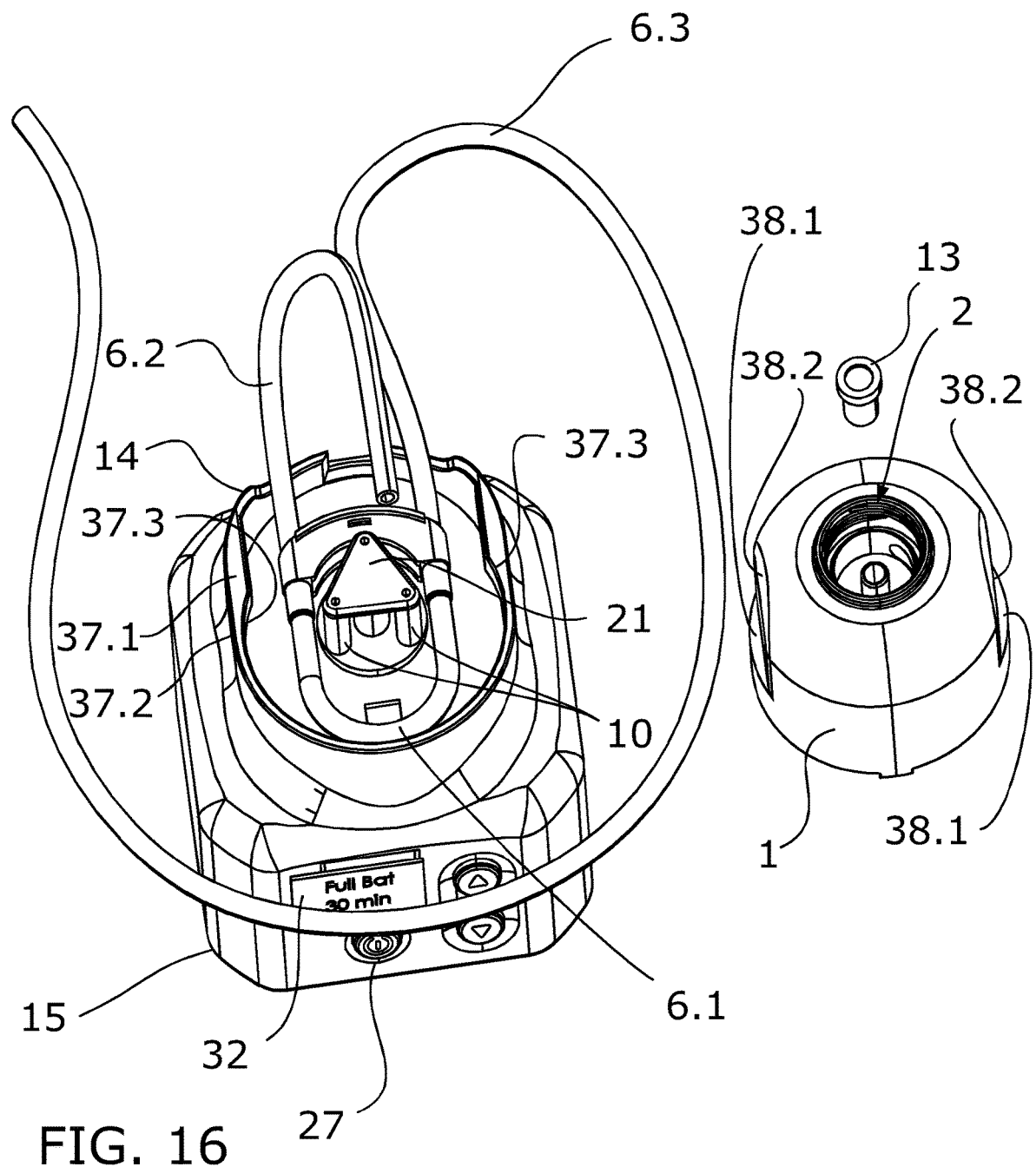
FIG. 16 shows the same view than FIG. 15 wherein the cap and the filtering means have been moved to one side in order to have visual access to the inner part where the rollers are located.

FIG. 16 shows the same view than FIG. 15 wherein the cap (1) and the filtering means (13) have been moved to one side in order to have visual access to the inner part of the driving head (8) where the rollers (10) are located. In this view, it can be seen that the first flexible conduit segment (6.1) is spaced away from the roller frame with the set of rollers (10).

In the second final locking position, the first flexible conduit segment (6.1) is pressed by the rollers (10) and, when the roller frame (21) is driven by the motor of the driving head (8) then the liquid conducted by the first flexible conduit segment (6.1) is being driven.

As it is shown in FIG. 17, the inner wall of the second frame segment (12) of the cap where the first flexible conduit segment (6.1) rests is a cylindrical surface, therefore, when the first flexible conduit segment (6.1) is pressed by the set of rollers (10) having a parallel rotational axis then no shear stress is generated in the first flexible conduit segment (6.1).

FIGS. 12 and 14 show the electronic system (31), particularly the groove configured for receiving a portion of the conduit (6), when said conduit is transparent, for determining when there is a change of light transmission properties through the conduit (6) by means of the optoelectric sensor (29). In this embodiment the groove is oriented horizontally in order to help the orientation of the tube. Said configuration also may be applied to the first embodiment.

The invention claimed is:

1. A closure cap for a container for supplying enteral feeding products contained in said container by means of a drive of a drive head, the cap being adapted for being coupled to the drive head, comprising:
    a first cavity suitable for receiving therein products coming from inside the container, the first cavity comprising a coupling means for an attachment of the cap with a neck of the container, a first outlet port of the first cavity, the first cavity defines a first opening;
    a second cavity separated from the first cavity wherein the second cavity defines a second opening in opposition to the first opening of the first cavity, the second cavity comprising
    a second outlet port of the cap for supplying the product of the container,
    a support seating,
    a conduit providing fluid communication between the first outlet port of the first cavity and the second outlet port of the second cavity, the conduit comprising a first flexible conduit segment with a first region which is supported on the support seating and a second region which is arranged facing the first region in the first flexible conduit segment so as to allow rotary rollers of the drive head to press the second region against the support seating, such that when the cap is in the operating mode with the drive head the fluid contained inside the conduit is driven by an action of the rollers.

2. The cap according to claim 1, wherein the first cavity is configured for receiving the neck of the container according to a longitudinal direction, and the first flexible conduit segment of the conduit containing the first region and the second region extends in a plane transverse to the longitudinal direction.

3. The cap-according to claim 2, wherein a main body of the cap is a frame comprising at least two frame segments extending according to the longitudinal direction:
    a first frame segment comprising the first cavity and the coupling means for attaching the cap with a neck of the container, and
    a second frame segment comprising the second cavity for housing the drive head.

4. The cap according to claim 3, wherein: the second frame segment has a larger diameter than the first frame segment, and in that both frame segments are connected by a disc perpendicular to the longitudinal direction;
    the cap comprises a casing which houses therein the first frame segment and is supported on a peripheral area of the disc; and the casing can be coupled to the second frame segment through clipping with the peripheral area of the disc.

5. The cap according to claim 3, wherein the second frame segment comprises at least one protrusion projecting in a radial direction with respect to the longitudinal direction to be fitted in at least one groove of the drive head, configuring a bayonet lock between the cap and the drive head.

6. The cap-according to claim 1, wherein the first flexible conduit segment of the conduit containing the first region and the second region has a directrix of a circular arc contained in a plane transverse to a longitudinal direction.

7. The cap according to claim 1, wherein:
    the support seating is a surface segment in a form of a band directrix of which extends in a circle around a central axis and in a plane transverse to a longitudinal direction, the central axis being parallel to the longitudinal direction, wherein a section of the surface segment according to a plane going through the central axis is an arc-shaped segment; and the arc-shaped segment has normal direction corresponding to a surface of the support seating that is oblique and oriented towards an outside of the second cavity.

8. The cap according to claim 1, wherein a radius of curvature of an arc-shaped segment of a section of a surface of the support seating is greater than a radius of curvature of a cross section of the conduit.

9. The cap according to claim 1, wherein the support seating is a surface segment in a form of a cylindrical band housed in the second cavity.

10. The cap according to claim 1, wherein the support seating is on an inner wall of a second frame segment.

11. The cap according to claim 1, wherein:

an exit of the first outlet port of the first cavity is outside a first frame segment, a second frame segment has a connection adaptor with an end inside the second cavity and an opposite end outside the second frame segment, and wherein the cap comprises a second fluid connection conduit between the first outlet port of the first cavity and an outer end of the connection adaptor, and the conduit is connected to an inner end of the connection adaptor for fluid communication with the first outlet port.

12. The cap according to claim 1, comprising a third fluid connection conduit between the second outlet port and a connector.

13. The cap according to claim 1, wherein: the cap further comprises linear guiding means perpendicular to a longitudinal direction to be fitted with opposite linear guiding means of the drive head, configuring a linear bayonet lock between the cap and the drive head; and the linear bayonet lock has a first insertion position and a final locking position; wherein in the final locking position, the rotary rollers of the drive head are exerting a pressing force against the first flexible conduit segment.

14. The cap according to claim 1 comprising a check valve for an entry of air from the second open cavity to the first open cavity.

15. The cap according to claim 1, wherein the first cavity comprises perforation means for perforating a seal of the neck of the container when the cap is coupled to the neck.

16. A drive system comprising the cap according to claim 1 and a drive head configured to be coupled to the cap for driving a supply of the enteral feeding products contained in the container through said cap when the cap is in an operating mode in the neck closing the container, the drive head comprising:

one or more rotary rollers radially distributed around an axis of rotation, operating means for operating the rotation of the one or more rotary rollers, coupling means for fixing the cap with respect to the drive head, such that when the drive head is coupled to the cap in the operating mode, the one or more rotary rollers are positioned with respect to the conduit of the cap such that the one or more rotary rollers exert pressure on a second region of a first flexible conduit segment of the cap to drive the products flowing through said conduit when the one or more rotary rollers rotate around the axis of rotation in the operating mode.

17. The drive system according to claim 16, wherein a main body of the drive head-comprises a casing comprising at least two casing segments extending according to a longitudinal direction, the at least two casing segment comprising:

a first casing segment being configured in a form of a cylindrical sector for housing the one or more rotary rollers, and a second casing segment being configured in a form of a closed cavity housing therein the operating means.

18. The drive system according to claim 16, wherein: the one or more rotary rollers are arranged on oblique shafts converging in the axis of rotation, the oblique shafts being fixed to a roller frame configured for rotating around the axis of rotation.

19. The drive system according to claim 16, comprising an optoelectronic sensor configured for detecting whether the products or air circulates through an inside of the conduit of the cap, such that when the drive head is in the operating mode with the cap and the optoelectronic sensor detects that air circulates through the inside of the conduit of the cap, rotation of the one or more rotary rollers is stopped.

* * * * *